US008633322B2

(12) United States Patent  
Parker et al.

(10) Patent No.: US 8,633,322 B2
(45) Date of Patent: Jan. 21, 2014

(54) ALKYNYL DERIVATIVES USEFUL AS DPP-1 INHIBITORS

(75) Inventors: Michael H. Parker, Chalfont, PA (US); Dennis J. Hlasta, Doylestown, PA (US); Yifang Huang, Lansdale, PA (US); Allen B. Reitz, Lansdale, PA (US); Edward C. Lawson, Pipersville, PA (US); Carsten Schubert, Phoenixville, PA (US); Eric Strobel, Warrington, PA (US); Brett A. Tounge, Blue Bell, PA (US); Kimberly White, North Wales, PA (US); Michael P. Winters, Morgantown, PA (US); Shyamali Ghosh, Norristown, PA (US)

(73) Assignee: Janssen Pharmaceutica NV (BE)

( * ) Notice: Subject to any disclaimer, the term of this patent is extended or adjusted under 35 U.S.C. 154(b) by 396 days.

(21) Appl. No.: 12/914,244

(22) Filed: Oct. 28, 2010

(65) Prior Publication Data

US 2011/0105562 A1 May 5, 2011

Related U.S. Application Data

(60) Provisional application No. 61/256,171, filed on Oct. 29, 2009.

(51) Int. Cl.
*A61K 31/445* (2006.01)
*C07D 211/40* (2006.01)

(52) U.S. Cl.
USPC .......................................... 546/216; 514/326

(58) Field of Classification Search
USPC .......................................... 514/326; 546/216
See application file for complete search history.

(56) References Cited

U.S. PATENT DOCUMENTS

| 4,847,241 A * | 7/1989 | Hansen et al. ................ 514/18.3 |
| 5,481,021 A | 1/1996 | Garland et al. |
| 2007/0155803 A1 | 7/2007 | Bondebjerg et al. |
| 2009/0012007 A1 | 1/2009 | Schmidt et al. |

FOREIGN PATENT DOCUMENTS

| DE | 4321502 A1 | 1/1995 |
| JP | 2002/145897 A | 5/2002 |
| WO | WO 93/12074 A1 | 6/1993 |
| WO | WO 97/03945 A1 | 2/1997 |
| WO | WO 97/08145 A1 | 3/1997 |
| WO | WO 2007/136921 A2 | 11/2007 |
| WO | WO 2007/136921 A3 | 11/2007 |
| WO | WO 2008/144544 A1 | 11/2008 |
| WO | WO 2009/026197 A1 | 2/2009 |
| WO | WO 2009/074829 A1 | 6/2009 |

OTHER PUBLICATIONS

Methot, N., et al., "In Vivo Inhibition of Serine Protease Processing Requires a High Fractional Inhibition of Cathepsin C", *Molecular Pharmacology*, 2008, pp. 1847-1865, vol. 73(6).
Greenspan, et al., "Identification of Structure-Based Drug Design", Journal of Medicinal Chemistry, American Chemical Society, Washington, US, Jan. 1, 2001, pp. 4524-4534, vol. 44.
International Search Report, PCT/US2010/054445, dated Feb. 15, 2011.

* cited by examiner

*Primary Examiner* — John Mabry
(74) *Attorney, Agent, or Firm* — Mary A. Appollina

(57) ABSTRACT

The present invention is directed to novel alkynyl derivatives, pharmaceutical compositions containing them and their use in the treatment of disorders and conditions modulated by DPP-1.

11 Claims, No Drawings

ALKYNYL DERIVATIVES USEFUL AS DPP-1 INHIBITORS

CROSS-REFERENCE TO RELATED APPLICATIONS

This application claims priority from U.S. Provisional Application Ser. Nos. 61/256,171 filed Oct. 29, 2009, the contents of each of which are hereby incorporated by reference in their entirety.

FIELD OF THE INVENTION

The present invention is directed to novel alkynyl derivatives, pharmaceutical compositions containing them and their use in the treatment of disorders and conditions modulated by DPP-1.

BACKGROUND OF THE INVENTION

Chronic Obstructive Pulmonary Disease (COPD) is characterized by the progressive development of irreversible airflow limitation. COPD consists of chronic obstructive bronchitis, with obstruction of small airways, and emphysema, with enlargement of air spaces and destruction of lung parenchyma, loss of lung elasticity, and closure of small airways. In COPD patients, there were increased numbers of neutrophils, cytotoxic T lymphocytes and macrophages in bronchoalveolar lavage (BAL) airways and lung parenchyma. The presence of these inflammatory cells is correlated well with severity of airway obstruction and alveolar wall destruction. It has been shown that neutrophil elastase; cathepsin G and proteinase 3 can produce emphysema and mucus hypersecretion in lab animals. Granzymes A & B are the neutral serine proteases that are expressed exclusively in the granules of activated cytotoxic T lymphocytes. In COPD the protease-antiprotease balance appears to be tipped in favor of increased proteolysis due to increase in polymorphonuclear neutrophil (PMN)-derived proteases, cathepsins and matrix metalloproteases (MMPs). Therefore, a drug that inhibits all or most of the relevant proteases mentioned above is expected to be effective in the treatment of COPD.

Dipeptidyl Peptidase-1 (DPP-1, cathepsin C) is a member of the lysosomal papain-type cysteine protease family that also includes cathepsin B, K, H, L, O, and S. DPP-1 (MW 200 kd) is composed of a dimer of disulfide-linked heavy and light chains, both from a single protein precursor. DPP-1 mRNA is highly expressed in tissues such as lung, spleen, kidney and liver; in inflammatory cells such as PMN, cytotoxic T lymphocytes, alveolar macrophages and mast cells. The biological function of DPP-1 is to convert inactive proenzymes into active enzyme by removing a dipeptide from N-terminal. The proenzymes that are activated by DPP-1 are PMN-derived proteases, granzymes A & B, chymase and tryptase. Since these enzymes play an important pathological role in COPD, inhibition of DDP-1 by small molecules would be a rational therapeutic intervention for COPD. Additional therapeutic indications for a DPP-1 inhibitor are asthma, rhinitis, and rheumatoid arthritis.

There remains a need for inhibitors of DPP-1 for the treatment of DPP-1 mediated disorders and conditions, including but not limited to rheumatoid arthritis, asthma, chronic obstructive pulmonary disease, sepsis, irritable bowel disease, cystic fibrosis, and abdominal aortic aneurism.

SUMMARY OF THE INVENTION

The present invention is directed to compounds of formula (I)

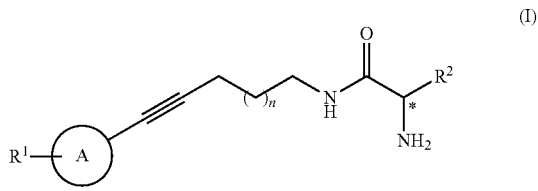

wherein
$R^1$ is selected from the group consisting of hydrogen, $C_{3-8}$cycloalkyl, phenyl, benzyloxy- and piperidinyl-oxy-;

is a ring structure selected from the group consisting of phenyl, naphthyl, fluorenyl, isoquinolinyl, benzofuryl, benzothiophenyl, benzo[1,3]dioxolyl and 2,3-dihydro-benzo[1,4]dioxinyl; wherein the

ring structure is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, ($C_{1-4}$alkoxy)-($C_{1-4}$alkyl)-, ($C_{1-4}$alkyl)-$SO_2$— and ($C_{1-4}$alkyl)-C(O)—NH—;
n is an integer selected from 0 and 1;
$R^2$ is selected from the group consisting of $C_{1-4}$alkyl, $C_{2-4}$alkenyl, $C_{2-4}$alkynyl, hydroxy substituted $C_{1-4}$alkyl, $NR^AR^B$—($C_{1-2}$alkyl)-, cyclopropyl-methyl-, benzyl- and heteroaryl-($CH_2$)$_{1-2}$; wherein $R^A$ and $R^B$ are each independently selected from hydrogen or $C_{1-4}$alkyl;
provided that $R^2$ is other than t-butyl;
and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by DPP-1 (cathepsin C) (selected from the group consisting of rheumatoid arthritis, asthma, chronic obstructive pulmonary disease, sepsis, irritable bowel disease, cystic fibrosis, and abdominal aortic aneurism) in a subject in need thereof comprising administering to the subject a therapeutically effective amount of any of the compounds or pharmaceutical compositions described above.

Another example of the invention is the use of any of the compounds described herein in the preparation of a medicament for treating: (a) rheumatoid arthritis, (b) asthma, (c) chronic obstructive pulmonary disease, (d) sepsis, (e) irritable bowel disease, (f) cystic fibrosis, or (g) abdominal aortic aneurism, in a subject in need thereof.

In another example, the present invention is directed to a compound as described herein for use in a methods for treating a disorder selected from the group consisting of rheumatoid arthritis, asthma, chronic obstructive pulmonary disease, sepsis, irritable bowel disease, cystic fibrosis, and abdominal aortic aneurism, in a subject in need thereof.

DETAILED DESCRIPTION OF THE INVENTION

The present invention is directed to a process for the preparation of compound of formula (I)

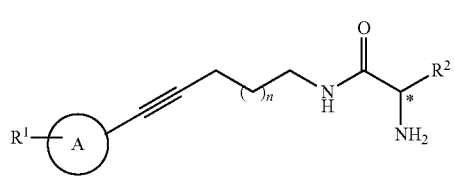

(I)

wherein $R^1$, $R^2$, n and

are as herein defined. The compounds of the present invention are inhibitors of DPP-1, useful in the treatment of disorders, diseases and conditions mediated by DPP-1 (cathepsin C), including, but not limited to, rheumatoid arthritis, asthma, chronic obstructive pulmonary disease, sepsis, irritable bowel disease, cystic fibrosis, and abdominal aortic aneurism.

In an embodiment of the present invention, $R^1$ is selected from the group consisting of hydrogen, $C_{5-6}$cycloalkyl, phenyl, benzyl-oxy- and piperidinyl-oxy-. In another embodiment of the present invention, $R^1$ is selected from the group consisting of hydrogen, $C_{5-6}$cycloalkyl, phenyl, benzyl-oxy, piperidin-4-yl-oxy and piperidin-3-yl-oxy.

In another embodiment of the present invention, $R^1$ is selected from the group consisting of hydrogen, 2-(cyclohexyl), 2-(phenyl), 3-(phenyl), 4-(benzyl-oxy), 3-(piperidin-4-yl-oxy), 3-(piperidin-3R-yl-oxy) and 3-(piperidin-3S-yl-oxy).

In another embodiment of the present invention, $R^1$ is selected from the group consisting of hydrogen, 2-(phenyl), 3-(phenyl), 4-(benzyl-oxy), 3-(piperidin-4-yl-oxy), 3-(piperidin-3R-yl-oxy) and 3-(piperidin-3S-yl-oxy). In another embodiment of the present invention, $R^1$ is selected from the group consisting of hydrogen, 3-(phenyl), 4-(benzyl-oxy), 3-(piperidin-4-yl-oxy), 3-(piperidin-3R-yl-oxy) and 3-(piperidin-3S-yl-oxy). In another embodiment of the present invention, $R^1$ is selected from the group consisting of hydrogen, 3-(phenyl) and 3-(piperidin-4-yl-oxy).

In an embodiment of the present invention, the $R^1$ group is bound to the

ring at the 2-, 3- or 4-position. In another embodiment of the present invention, the $R^1$ group is bound to the

ring at the 3- or 4-position. In another embodiment of the present invention, the $R^1$ group is bound to the

ring at the 3-position.

In an embodiment of the present invention,

is a ring structure selected from the group consisting of phenyl, naphthyl, fluorenyl, isoquinolinyl, benzofuryl, benzothiophenyl, benzo[1,3]dioxolyl and 2,3-dihydro-benzo[1,4]dioxinyl; wherein the

ring structure is optionally substituted with one to four substituents independently selected from the group consisting of halogen, hydroxy, $C_{1-4}$alkyl, fluorinated $C_{1-4}$alkyl, $C_{1-4}$alkoxy, $(C_{1-4}$alkoxy)-$(C_{1-4}$alkyl)-, $(C_{1-4}$alkyl)-$SO_2$— and $(C_{1-4}$alkyl)-C(O)—NH—. In another embodiment of the present invention,

is a ring structure selected from the group consisting of phenyl, naphthyl, 9H-fluorenyl, isoquinolinyl, benzofuryl, benzothiophenyl, benzo[1,3]dioxolyl and 2,3,-dihydro-benzo[1,4]dioxinyl; wherein the phenyl or naphth-1-yl is optionally substituted with one to four substituent independently selected from the group consisting of hydroxy, halogen, $C_{1-4}$alkyl, $C_{1-2}$alkoxy, trifluoromethyl, $(C_{1-2}$alkoxy)-$(C_{1-2}$alkyl)-, $C_{1-2}$alkyl-$SO_2$— and $C_{1-2}$alkyl-C(O)—NH—.

In another embodiment of the present invention,

is a ring structure selected from the group consisting of phenyl, 2-hydroxy-phenyl, 4-isopropyl-phenyl, 2-methoxy-phenyl, 3-methoxy-phenyl, 4-methoxy-phenyl, 5-methoxy-phenyl, 2-trifluoromethyl-phenyl, 3-trifluoromethyl-phenyl, 4-trifluoromethyl-phenyl, 4-methyl-sulfonyl-phenyl, 2-methyl-carbonyl-amino-phenyl, 4-methyl-carbonyl-amino-phenyl, 2,3-difluoro-phenyl, 3,4-difluoro-phenyl, 2,6-dimethyl-phenyl, 3,5-dimethyl-phenyl, 3,6-dimethyl-phenyl, 3,4-dimethoxy-phenyl, 3,5-dimethoxy-phenyl, 2,4,6-trimethyl-phenyl, 2,3,5,6,-tetramethyl-phenyl, naphth-1-yl, naphtha-2-yl, 2-hydroxy-naphth-1-yl, 2-fluoro-naphth-1-yl, 4-fluoro-naphth-1-yl, 4-methyl-naphth-1-yl, 2-methoxy-naphth-1-yl, 2-(methoxy-methyl)-naphth-1-yl, 9H-fluoren-2-yl, isoquinolin-4-yl, isoquinolin-5-yl, benzofur-5-yl, benzothiophen-5-yl, benzo[1,3]dioxol-5-yl and 2,3,-dihydro-benzo[1,4]dioxin-6-yl. In another embodiment of the present invention,

is a ring structure selected from the group consisting of phenyl, 2-hydroxy-phenyl, 4-isopropyl-phenyl, 3-methoxy-phenyl, 4-methoxy-phenyl, 5-methoxy-phenyl, 3-trifluoromethyl-phenyl, 2-methyl-carbonyl-amino-phenyl, 4-methyl-carbonyl-amino-phenyl, 2,3-difluoro-phenyl, 3,4-difluoro-phenyl, 2,6-dimethyl-phenyl, 3,5-dimethyl-phenyl, 2,4,6-trimethyl-phenyl, naphth-1-yl, 2-fluoro-naphth-1-yl, 4-fluoro-naphth-1-yl, 4-methyl-naphth-1-yl, 9H-fluoren-2-yl, isoquinolin-5-yl, benzofur-5-yl, benzothiophen-5-yl and 2,3,-dihydro-benzo[1,4]dioxin-6-yl. In another embodiment of the present invention,

is a ring structure selected from the group consisting of phenyl, 4-isopropyl-phenyl, 4-methoxy-phenyl, 5-methoxy-phenyl, 3,4-difluoro-phenyl, 2,6-dimethyl-phenyl, 3,5-dimethyl-phenyl, naphth-1-yl, and 9H-fluoren-2-yl. In another embodiment of the present invention,

is a ring structure selected from the group consisting of phenyl, 4-methoxy-phenyl and 3,4-difluoro-phenyl.

In an embodiment of the present invention n is 0. In another embodiment of the present invention n is 1.

In an embodiment of the present invention, the stereo-center denoted with the "*" symbol, in the compounds of formula (I) is present in the (S)-configuration. In another embodiment of the present invention, the stereo-center denoted with the "*" symbol, in the compounds of formula (I) is present in the (R)-configuration.

In an embodiment, the present invention is directed to a compound of formula (I) wherein the starred stereo-center is present in either the (S)-stereo-configuration in an enantiomeric excess of greater than or equal to about 80%, more preferably, in an enantiomeric excess of greater than or equal to about 90%, more preferably still, in an enantiomeric excess of greater than or equal to about 95%, more preferably still, in an enantiomeric excess of greater than or equal to about 98%, most preferably, in an enantiomeric excess of greater than or equal to about 99%.

In another embodiment, the present invention is directed to a compound of formula (I) wherein the starred stereo-center is present in either the (R)-stereo-configuration in an enantiomeric excess of greater than or equal to about 80%, more preferably, in an enantiomeric excess of greater than or equal to about 90%, more preferably still, in an enantiomeric excess of greater than or equal to about 95%, more preferably still, in an enantiomeric excess of greater than or equal to about 98%, most preferably, in an enantiomeric excess of greater than or equal to about 99%.

In an embodiment of the present invention, $R^2$ is selected from the group consisting of $C_{1-4}$alkyl, $C_{2-4}$alkenyl, $C_{2-4}$alkynyl, hydroxy substituted $C_{2-4}$alkyl, $NR^A R^B$—($C_{1-2}$alkyl)-, cyclopropyl-methyl-, benzyl- and heteroaryl-($C_{1-4}$alkyl)-; wherein the heteroaryl is selected from the group consisting of pyridyl, pyrazolyl, imidazolyl and thienyl; and wherein $R^A$ and $R^B$ are each independently selected from hydrogen or $C_{1-2}$alkyl; provided that $R^2$ is other than t-butyl. In another embodiment of the present invention, $R^2$ is selected from the group consisting of $C_{1-4}$alkyl, hydroxy substituted $C_{1-2}$alkyl, $C_{2-4}$alkenyl, $C_{2-4}$alkynyl, $NH_2$—($C_{1-2}$alkyl)-, cyclopropyl-methyl-, benzyl-, pyrazol-1-yl-methyl-, imidazol-4-yl-methyl-, pyrid-2-yl-methyl-, pyrid-3-yl-methyl- and thien-2-yl-methyl-; provided that $R^2$ is other than t-butyl.

In another embodiment of the present invention, $R^2$ is selected from the group consisting of ethyl, n-propyl, isopropyl, n-butyl, isobutyl, hydroxy-methyl, hydroxy-ethyl, n-buten-3-yl, propyn-2-yl, amino-n-propyl-, cyclopropyl-methyl, benzyl, pyrazol-1-yl-methyl-, imidazol-4-yl-methyl-, pyrid-2-yl-methyl-, pyrid-3-yl-methyl- and thien-2-yl-methyl-. In another embodiment of the present invention, $R^2$ is selected from the group consisting of ethyl, n-propyl, n-butyl, hydroxy-ethyl, n-buten-3-yl, propyn-2-yl, pyrazol-1-yl-methyl-, imidazol-4-yl-methyl-, and thien-2-yl-methyl-. In another embodiment of the present invention, $R^2$ is selected from the group consisting of ethyl, n-propyl, hydroxy-ethyl, n-buten-3-yl, propyn-2-yl, imidazol-4-yl-methyl- and thien-2-yl-methyl-. In another embodiment of the present invention, $R^2$ is selected from the group consisting of ethyl, propyn-2-yl, imidazol-4-yl-methyl- and thien-2-yl-methyl-.

Additional embodiments of the present invention, include those wherein the substituents selected for one or more of the variables defined herein (i.e. $R^1$, $R^2$,

)

and are independently selected to be any individual substituent or any subset of substituents selected from the complete list as defined herein. In another embodiment of the present invention is any single compound or subset of compounds selected from the representative compounds listed in Table 1 below.

Representative compounds of the present invention are as listed in Table 1 below. In the listing of the substituents for the $R^1$ group, the number in front of the parentheses containing the $R^1$ substituent group indicates the position at which the $R^1$ group is bound on the ring. For example, the group "3-(piperidin-4-yl-oxy-)" shall denote a group of the following structure:

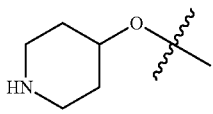

bound at the 3-position of the

ring (wherein the 1-position of the

ring is the binding position of the

ring to the rest of the compound of formula (I)).

TABLE 1

Representative Compounds of Formula (I)

| ID No | R[1] | A | n | * | R[2] |
|---|---|---|---|---|---|
| 1 | 3-(piperidin-4-yl-oxy) | phenyl | 1 | S | benzyl |
| 3 | 3-(piperidin-4-yl-oxy) | phenyl | 1 | S | propyn-2-yl |
| 6 | 3-(piperidin-4-yl-oxy) | phenyl | 0 | S | propyn-2-yl |
| 7 | 3-(piperidin-4-yl-oxy) | 5-methoxy-phenyl | 1 | S | propyn-2-yl |
| 8 | 3-(piperidin-4-yl-oxy) | phenyl | 1 | S | n-buten-3-yl |
| 9 | 3-(piperidin-4-yl-oxy) | phenyl | 1 | S | ethyl |
| 11 | 3-(piperidin-4-yl-oxy) | phenyl | 1 | S | cyclopropyl-methyl- |
| 12 | 3-(piperidin-4-yl-oxy) | phenyl | 1 | S | n-butyl |
| 13 | 3-(piperidin-4-yl-oxy) | phenyl | 1 | S | amino-n-propyl- |
| 15 | 3-(piperidin-4-yl-oxy) | phenyl | 1 | S | hydroxy-ethyl- |
| 16 | 3-(piperidin-4-yl-oxy) | phenyl | 1 | S | isopropyl |
| 18 | 3-(piperidin-4-yl-oxy) | phenyl | 1 | S | n-propyl |
| 19 | 3-(piperidin-4-yl-oxy) | phenyl | 1 | S | pyrazol-1-yl-methyl- |
| 20 | 3-(piperidin-4-yl-oxy) | phenyl | 1 | S | imidazol-4-yl-methyl- |
| 24 | 3-(phenyl) | phenyl | 1 | S | propyn-2-yl- |
| 25 | 3-(piperidin-4-yl-oxy) | phenyl | 1 | S | hydroxy-methyl- |
| 31 | 3-(piperidin-4-yl-oxy) | phenyl | 1 | S | isobutyl |
| 33 | 3-(piperidin-4-yl-oxy) | phenyl | 1 | S | pyrid-3-yl-methyl- |
| 35 | H | 3-methoxy-phenyl | 1 | S | ethyl |
| 39 | H | 3,4-difluoro-phenyl | 1 | S | ethyl |
| 40 | H | 4-methoxy-phenyl | 1 | S | ethyl |
| 41 | H | naphth-1-yl | 1 | S | ethyl |
| 49 | H | 2,6-dimethyl-phenyl | 1 | S | ethyl |
| 51 | H | benzo[1,3]-dioxol-5-yl | 1 | S | ethyl |
| 55 | H | 2,4,6-trimethyl-phenyl- | 1 | S | ethyl |
| 56 | H | 4-methyl-sulfonyl-phenyl | 1 | S | ethyl |
| 57 | H | 3,4-dimethoxy-phenyl | 1 | S | ethyl |
| 58 | H | 4-trifluoro-methyl-phenyl | 1 | S | ethyl |
| 59 | H | 3,5-dimethoxy-phenyl | 1 | S | ethyl |
| 60 | H | benzo-thiophen-5-yl | 1 | S | ethyl |
| 61 | 2-(phenyl) | phenyl | 1 | S | ethyl |
| 63 | 3-(piperidin-4-yl-oxy) | phenyl | 1 | S | thien-2-yl-methyl- |
| 71 | 3-(piperidin-4-yl-oxy) | phenyl | 1 | R | ethyl |
| 72 | H | 3-trifluoro-methyl-phenyl | 1 | S | ethyl |
| 73 | H | naphth-2-yl | 1 | S | ethyl |
| 74 | H | 2-trifluoro-methyl-phenyl | 1 | S | ethyl |
| 75 | 2-(cyclohexyl) | phenyl | 1 | S | ethyl |
| 76 | H | 2,3,5,6-tetra-methyl-phenyl | 1 | S | ethyl |
| 77 | H | 3,6-dimethyl-phenyl | 1 | S | ethyl |
| 78 | 3-(piperidin-3R-yl-oxy) | phenyl | 1 | S | ethyl |
| 79 | 3-(piperidin-3R-yl-oxy) | phenyl | 1 | S | propyn-2-yl |
| 80 | 3-(piperidin-3S-yl-oxy) | phenyl | 1 | S | ethyl |
| 81 | 4-(phenyl) | phenyl | 1 | S | ethyl |
| 82 | H | isoquinolin-5-yl | 1 | S | ethyl |
| 83 | H | 4-methyl-naphth-1-yl | 1 | S | ethyl |
| 84 | H | 4-fluoro-naphth-1-yl | 1 | S | ethyl |
| 85 | 3-(piperidin-3S-yl-oxy) | phenyl | 1 | S | propyn-2-yl |
| 86 | 4-(benzyl-oxy) | phenyl | 1 | S | ethyl |
| 87 | H | 2-methoxy-naphth-1-yl | 1 | S | ethyl |

TABLE 1-continued

Representative Compounds of Formula (I)

| ID No | R¹ | A | n | * | R² |
|---|---|---|---|---|---|
| 88 | H | 2-(methoxy-methyl-naphth-1-yl) | 1 | S | ethyl |
| 89 | H | isoquinolin-4-yl | 1 | S | ethyl |
| 90 | 3-(piperidin-4-yl-oxy) | phenyl | 1 | S | pyrid-2-yl-methyl- |
| 91 | H | benzofur-5-yl | 1 | S | ethyl |
| 92 | H | 3-methoxy-phenyl | 1 | R | ethyl |
| 95 | H | 4-isopropyl-phenyl | 1 | S | ethyl |
| 96 | H | 3,5-dimethyl-phenyl | 1 | S | ethyl |
| 97 | H | 2,3-dihydro-benzo[1,4]-dioxin-6-yl | 1 | S | ethyl |
| 98 | H | phenyl | 1 | S | ethyl |
| 99 | H | 2-methoxy-phenyl | 1 | S | ethyl |
| 100 | H | 4-methyl-carbonyl-amino-phenyl | 1 | S | ethyl |
| 101 | H | 9H-fluoren-2-yl | 1 | S | ethyl |
| 102 | H | 2,3-difluoro-phenyl | 1 | S | ethyl |
| 103 | H | 2-methyl-carbonyl-amino-phenyl | 1 | S | ethyl |
| 104 | H | 2-hydroxy-phenyl | 1 | S | ethyl |
| 105 | H | 2-hydroxy-naphth-1-yl | 1 | S | ethyl |
| 106 | H | 2-fluoro-naphth-1-yl | 1 | S | ethyl |

As used herein, "halogen" shall mean chlorine, bromine, fluorine and iodine.

As used herein, the term "alkyl" whether used alone or as part of a substituent group, shall include straight and branched carbon chain compositions of one to six carbon atoms. For example, alkyl radicals include methyl, ethyl, propyl, isopropyl, butyl, isobutyl, sec-butyl, t-butyl, n-pentyl, and the like. The prefix "$C_{X-Y}$" wherein X and Y are integers, when used with alkyl shall mean a carbon chain composition of between X and Y carbon atoms. For example, the term "$C_{1-4}$alkyl" shall mean a straight or branched carbon chain composition of 1 to 4 carbon atoms.

One skilled in the art will recognize that the terms "-(alkyl)-" and "—($C_{1-4}$alkyl)-" shall denote any alkyl or $C_{1-4}$alkyl carbon chain as herein defined, wherein said alkyl or $C_{1-4}$alkyl chain is divalent and is further bound through two points of attachment, preferably through two terminal carbon atoms.

As used herein, the term "alkenyl" whether used alone or as part of a substituent group, shall include straight and branched chains compositions of between 2 and 6 carbon atoms containing at least one unsaturated double bond. For example, alkenyl radicals include ethenyl, n-propen-2-yl, n-buten-2-yl, n-penten-2-yl and the like. The term "$C_{2-4}$alkenyl" shall mean a straight or branched carbon chain composition of 2 to 4 carbon atoms containing at least one unsaturated double bond.

As used herein, the term "alkynyl" whether used alone or as part of a substituent group, shall include straight and branched chains compositions of between 2 and 6 carbon atoms containing at least one unsaturated triple bond. For example, alkynyl radicals include ethynyl, n-propy-2-nyl, n-buty-2-nyl, n-penty-2-nyl and the like. The term "$C_{2-4}$alkynyl" shall mean a straight or branched carbon chain composition of 2 to 4 carbon atoms containing at least one unsaturated triple bond.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CCl_3$, —$CH_2$—$CF_3$, —$CH_2$—$CCl_3$, —$CF_2$—$CF_2$—$CF_2$—$CF_3$, and the like. Similarly, unless otherwise noted, the term "fluorinated $C_{1-4}$alkyl" shall mean any $C_{1-4}$alkyl group as defined above substituted with at least one fluoro atom, preferably substituted with a least one fluoro atom. Suitable examples include but are not limited to —$CF_3$, —$CH_2$—$CF_3$, —$CF_2$—$CF_2$—$CF_2$—$CF_3$, and the like.

As used herein, unless otherwise noted, the term "hydroxy substituted $C_{1-4}$alkyl" shall mean any $C_{1-4}$alkyl group as defined above substituted with at least one hydroxy group. Preferably, the $C_{1-4}$alkyl group is substituted with one hydroxy group. Preferably, the $C_{1-4}$alkyl group is substituted with a hydroxy group at a terminal carbon. Suitable examples include, but are not limited to, —$CH_2$(OH), —$CH_2$—$CH_2$(OH), —$CH_2$—CH(OH)—$CH_2$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. The prefix "$C_{X-Y}$" wherein X and Y are integers, when used with alkoxy, shall mean an ether radical of a straight or branched carbon chain composition of between X and Y carbon atoms. For example, the term "$C_{1-4}$alkoxy" shall mean an ether radical of a straight or branched carbon chain composition of 1 to 4 carbon atoms.

One skilled in the art will recognize that the terms "-(alkoxy)-" and "—($C_{1-4}$alkoxy)-" shall denote any alkoxy or $C_{1-4}$alkoxy group as herein defined, wherein said alkoxy or $C_{1-4}$alkoxy chain is divalent and is further bound through two points of attachment, preferably through a terminal carbon and the oxygen atoms.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —$OCF_3$, —$OCCl_3$, —$OCH_2$—$CF_3$, —$OCH_2$—$CCl_3$, —$OCF_2$—$CF_2$—$CF_2$—$CF_3$, and the like. Similarly, unless otherwise noted, the term "fluorinated $C_{1-4}$alkoxy" shall mean any $C_{1-4}$alkoxy group as defined above substituted with at least one fluoro atom, preferably substituted with a least one fluoro atom. Suitable examples include but are not limited to —$OCF_3$, —$OCH_2$—$CF_3$, —$OCF_2$—$CF_2$—$CF_2$—$CF_3$, and the like.

As used herein, unless otherwise noted, "aryl" shall refer to unsubstituted carbocylic aromatic groups such as phenyl, naphthyl, fluorenyl, and the like; preferably phenyl or naphthyl.

As used herein, unless otherwise noted, the term "$C_{3-8}$cycloalkyl" shall mean any stable 3-6 membered monocyclic, saturated ring system, for example cyclopropyl, cyclobutyl, cyclopentyl, cyclohexyl, cycloheptyl and cyclooctyl. One skilled in the art will recognize that the prefix "$C_{X-Y}$" when used with the term cycloalkyl shall denote the number of ring carbon atoms.

As used herein, unless otherwise noted, "heteroaryl" shall denote any five or six membered monocyclic aromatic ring structure containing between one and two heteroatoms independently selected from the group consisting of O, N and S.

The heteroaryl group may be attached at any heteroatom or carbon atom of the ring such that the result is a stable structure. Suitably examples include, but are not limited to pyrrolyl, pyrazolyl, furyl, thienyl, oxazolyl, imidazolyl, isoxazolyl, isothiazolyl, pyridyl, pyridazinyl, pyrimidinyl, pyrazinyl, pyranyl, furazanyl, and the like. Preferred heteroaryl groups include thienyl, pyrazolyl, pyridyl and imidazolyl.

When a particular group is "substituted" (e.g., alkyl, cycloalkyl, aryl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl-" substituent refers to a group of the formula

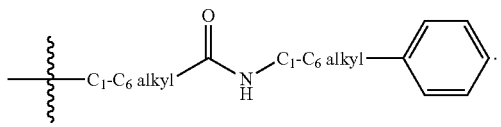

Abbreviations used in the specification, particularly the Schemes and Examples, are as follows:
Boc or BOC=tert-Butoxycabronyl
Cbz=Carboxy-benzyl
DCM=Dichloromethane
DIAD=Diisopropyl azodicarboxylate
DIPEA or DIEA=Diisopropylethylamine
DMAP=4-N,N-Dimethylaminopyridine
DME=Dimethyl ether
DMF=N,N-Dimethylformamide
DMSO=Dimethylsulfoxide
DTT=Dithiothreitol
EDC or EDCl=1-ethyl-3-(3-dimethylaminopropyl) carbodiimide
EtOAc=Ethyl Acetate
GR-AMC=Glycine-Arginine-amino-4-methyl-coumain
GSH=Glutathione
HATU=O-(7-Azabenzotriazol-1-yl)-N,N,N'',N''-Tetramethyl Uronium Hexafluorophosphate
HBTU=O-(1H-Benzotriazol-1-yl)-N,N,N',N'-tetramethyluronium hexafluorophosphate
HEPES=4-(2-Hydroxyethyl)-1-Piperizine Ethane Sulfonic Acid
HOBT or HOBt=1-Hydroxybenzotriazole
HPLC=High Pressure Liquid Chromatography
MeOH=Methanol
MOM=Methoxymethyl
MTBE=Methyl tert-Butyl Ether
NMP=N-methyl-2-pyrrolidinone
$Pd_2(OAc)_2$=Palladium(II)acetate
$Pd(dppf)Cl_2$=Dichloro[1,1'-bis(diphenylphosphine) ferrocene]palladium(II)
$Pd(dppp)Cl_2$=Bis(diphenylphosphino)propane palladium (II) chloride
$Pd(PPh_3)_4$=Tetrakistriphenylphosphine palladium (0)
$Pd(PPh_3)_2Cl_2$=Bis(triphenylphosphine)palladium (II) chloride
TEA=Triethylamine
TFA=Trifluoroacetic Acid
THF=Tetrahydrofuran
THP=Tetrahydropyranyl
TMS=Trimethylsilyl As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "DPP-1 mediated disorder" shall include any condition, disease or disorder which may be mediated through inhibition of DPP-1 activity. One skilled in the art will recognize that disorders mediated by DPP-1 include, but are not limited to (a) disorders of the respiratory tract: including obstructive diseases of the airways including asthma, including bronchial, allergic, intrinsic, extrinsic, exercise-induced, drug induce (including aspirin and NSAID-induced) and dust induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sacroidosis; farmer's lung and related diseases; hypersensitive pnemonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vascullitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

(b) skin disorders: psoriasis, atopic dermatitis, contact dermatatis or other eczematous deramtoses, and delayed-type hypersensitivity reactions; phyto- and photodermatitis; seborrhoeic dermatistis, dermatitis herptiformis, lichen planus, lichen slerosus et atrophica, pyoderma gangrenosum, skin sarcoid, discoid lupus erythematosus, pemphigus, pemphigoid, epidermolysis bullosa, urticaria, angioderma, vasculitides, toxid erythams, cutaceous eosinopiliass, alopecia greata, male-pattern baldness, Sweet's syndrome, Weber-Christian syndrome, erythema multiforma; cellulitis, both infective and non-infective; panniculitis; cutaceous lymphomas, non-melanoma skin cancer and other dysplastic lesions; drug-induced disorders including fixed-drug eruptions;

(c) eye disorders: blepharitis, conjunctivitis, including perennial and vernal allergic conjunctivitis; iritis; anterior and posterior uveitis; choroiditis; autoimmune, degenerative or inflammatory disorders affecting the retina; opthalmitis including sympathetic opthalmitis; sarcoidosis; infections including viral, fugal and bacterial;

(d) genitourinary disorders: nephritis including interstitial and glomerulnephritis; nephritic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction;

(e) allograft rejection disorders: acute and chronic following, for example, transplantation of kidney, heart, liver, lung, bone marrow, skin or cornea or following blood transfusion; or chronic graft versus host disease;

(f) auto-immune and allergic disorders including rheumatoid arthritis, irritable bowel syndrome, systemic lupus erythematosus, multiple sclerosis, Hashimoto's thyroiditis, Grave's disease, Addison's disease, diabetes mellitus, idiopathic thrombocytopaenic purpura, eosinophilic fasciitis, hyper-IgE syndrome, antiphospholipid syndrome and Sazary syndrome;

(g) cancers: including treatment of common cancers including prostate, breast, lung, ovarian, pancreatic, bowel and colon, stomach, skin and brain tumors and malignancies affecting the bone marrow (including leukaemias) and lymphoproliferative systems, such as Hodgkin's and non-Hodgkin's lymphoma; including the prevention and treatment of metastatic disease and tumor recurrences, and paraneoplstic syndrome; and (h) infectious diseases: viral diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoser virus (VZV), rhinovirus, adenovirus, coronavirus, influenza, parainfluenza; bacterial diseases such as tubercuavium, leprosy; other infectious diseases such as fungal diseases, Chlamydia, candida, aspergillus, cryptococcal meningitis, pneumocystis carnii, cryptosporidiosis, histoplasmosis, toxoplasmosis, trypanosome infection and leishmaniasis.

In another embodiment, the present invention is directed to methods for the treatment and/or prevention of a DDP-1 mediated disorder; wherein the DPP-1 mediated disorder is selected from the group consisting of chronic obstructive pulmonary disease (COPD), asthma, acute lung injury, adult respiratory distress syndrome, abdominal or thoracic aneurism, rheumatoid arthritis, osteoarthritis, multiple sclerosis, sepsis and taxoplasmosis.

In another embodiment, the present invention is directed to methods for the treatment and/or prevention of a DDP-1 mediated disorder; wherein the DPP-1 mediated disorder is selected from the group consisting of rheumatoid arthritis, asthma, chronic obstructive pulmonary disease (COPD), sepsis, irritable bowel disease, cystic fibrosis, and abdominal aortic aneurism.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max]) \times 100.$$

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "*Design of Prodrugs*", ed. H. Bundgaard, Elsevier, 1985.

Compounds of formula (I) may be prepared according to the process outlined in Scheme 1.

Scheme 1

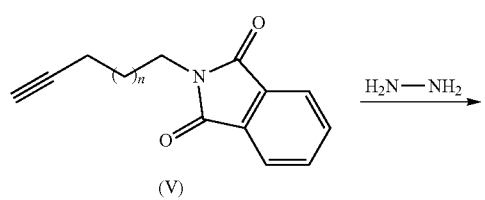

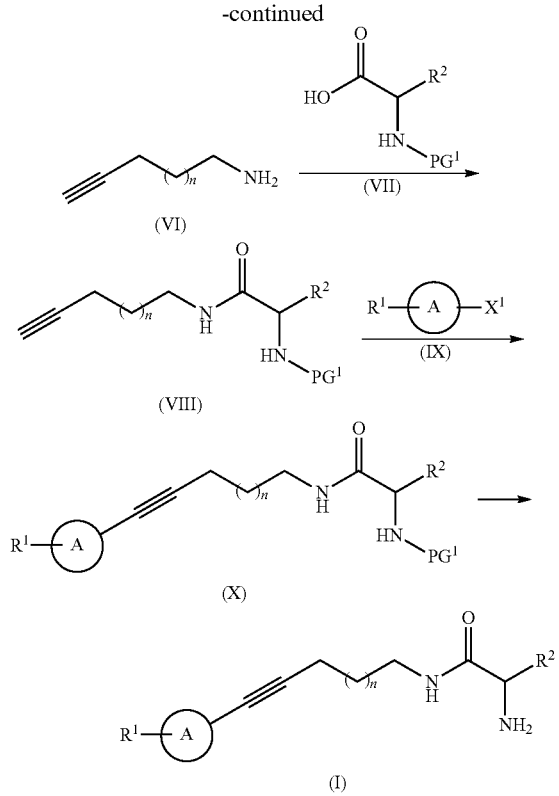

Accordingly, a suitably substituted compound of formula (V), a known compound or compound prepared by known methods, is reacted with hydrazine, a known compound; in a suitably selected alcohol such as methanol, ethanol, isopropanol, and the like; to yield the corresponding compound of formula (VI).

The compound of formula (VI) is reacted with a suitably substituted compound of formula (VII), wherein $PG^1$ is a suitably selected nitrogen protecting group such as BOC, —C(O)—CF$_3$, and the like; in the presence of a suitably selected coupling agent such as HOBt in combination with EDC, HATU, and the like; in the presence of an organic base such as TEA, DIPEA, pyridine, and the like; in the presence of a suitably selected catalyst such as DMAP, and the like; in a suitably selected organic solvent or mixture thereof such as DMF, NMP, and the like; to yield the corresponding compound of formula (VIII).

The compound of formula (VIII) is reacted with a suitably substituted compound of formula (IX), wherein $X^1$ is a suitably selected leaving group such as bromo, iodo, triflate, and the like; in the presence of a suitably selected catalysts such as Ph(PPh$_3$)$_2$Cl$_2$, Pd(OAc)$_2$Cl$_2$, Pd(dppf)Cl$_2$, Pd(dppp)Cl$_2$, and the like; preferably in the presence of CuI; in the presence of a base such as TEA, DIPEA, pyridine, and the like; in a suitably selected organic solvent such as DMF, NMP, and the like; at a temperature in the range of from about 50° C. to about 100° C., for example at about 70° C.; to yield the corresponding compound of formula (X).

The compound of formula (X) is de-protected according to known methods, to yield the corresponding compound of formula (I). For example, wherein $PG^1$ is —C(O)—CF$_3$, the compound of formula (X) may be de-protected by reacting with a suitably selected base such as NaOH, KOH, and the like; in a suitably selected organic solvent or mixture thereof such as THF, methanol, ethanol, and the like. Alternatively, wherein PG¹ is BOC and the like, the compound of formula (X) may be de-protected by reacting with a suitably selected acid such as HCl, TFA, and the like, in a suitably selected organic solvent or mixture thereof such as DCM, 1,4-dioxane, and the like.

Compounds of formula (I) (for example, compounds of formula (I) wherein R¹ is a piperidinyl-oxy-group) may alternatively be prepared according to the process outlined in Scheme 2 below.

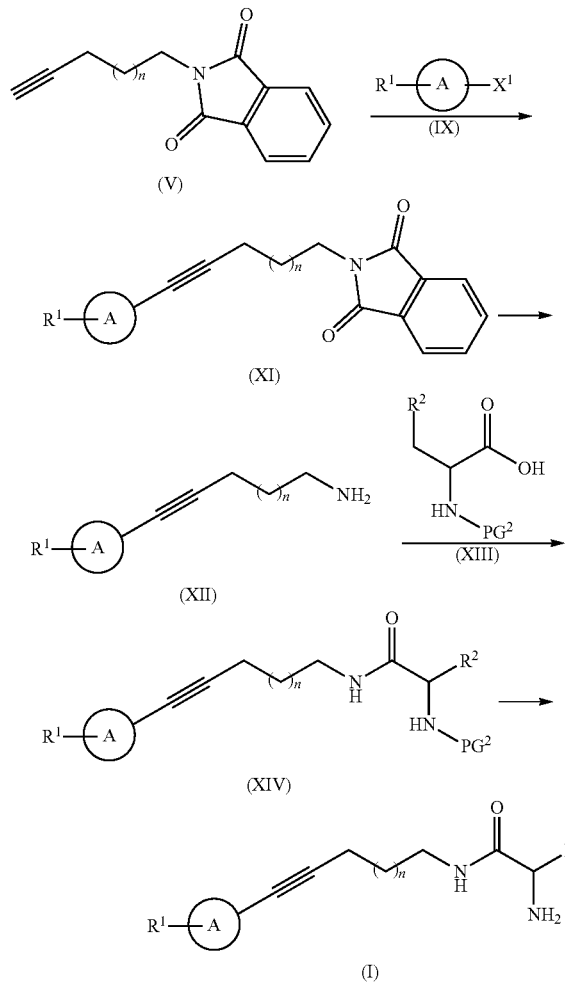

Accordingly, a suitably substituted compound of formula (V), a known compound or compound prepared by known methods, is reacted with a suitably substituted compound of formula (IX), wherein X¹ is a suitably selected leaving group such as bromo, iodo, triflate, and the like; in the presence of a suitably selected catalysts such as $Ph(PPh_3)_2Cl_2$, $Pd(OAc)_2Cl_2$, $Pd(dppf)Cl_2$, $Pd(dppp)Cl_2$, and the like; preferably in the presence of CuI; in the presence of a base such as TEA, DIPEA, pyridine, and the like; in a suitably selected organic solvent such as DMF, NMP, and the like; at a temperature in the range of from about 50° C. to about 100° C., for example at about 70° C.; to yield the corresponding compound of formula (XI).

The compound of formula (XI) is reacted with hydrazine, a known compound; in a suitably selected alcohol such as methanol, ethanol, isopropanol, and the like, to yield the corresponding compound of formula (XII).

The compound of formula (XII) is reacted with a suitably substituted compound of formula (XIII), a known compound or compound prepared by known methods; in the presence of a suitably selected coupling agent such as HBTU, HATU, HOBt in combination with EDC, and the like; in the presence of a suitably selected organic base such as TEA, DIPEA, pyridine, and the like; in the presence d a catalyst such as DMAP, and the like; in a suitably selected organic solvent such as DMF, NMP, and the like; to yield the corresponding compound of formula (XIV).

The compound of formula (XIV) is de-protected according to known methods, to yield the corresponding compound of formula (I). For example, wherein PG² is —C(O)—CF₃, the compound of formula (XIV) may be de-protected by reacting with a suitably selected base such as NaOH, KOH, and the like; in a suitably selected organic solvent or mixture thereof such as THF, methanol, ethanol, and the like. Alternatively, wherein PG² is BOC and the like, the compound of formula (XIV) may be de-protected by reacting with a suitably selected acid such as HCl, TFA, and the like, in a suitably selected organic solvent or mixture thereof such as DCM, 1,4-dioxane, and the like.

One skilled in the art will recognize that wherein the compound of formula (I), the R¹ group is piperidin-3-yl-oxy or piperidin-4-yl-oxy, then in the compound of formula (IX), the nitrogen on the 1-position of the piperidinyl group is preferably protected with a suitably selected nitrogen protecting group such as BOC, —C(O)—CF₃, CBz, and the like; that said nitrogen protecting group is maintained on the nitrogen through the reaction steps as outlined above; and further that said nitrogen protecting group is removed, according to known methods, either simultaneous with the removal of the PG² group or sequentially before or after removal of the PG² group.

For example, wherein R¹ is piperidin-3-yl-oxy or piperidin-4-yl-oxy, the nitrogen atom of the piperidinyl ring may be protected with a BOC group, which BOC group may be removed (simultaneously or sequentially with the removal of the PG² group) by reacting with a suitably selected acid such as HCl, TFA, and the like, in a suitably selected organic solvent such as DMF, and the like.

Compounds of formula (I) may alternatively be prepared according to the process outlined in Scheme 3 below.

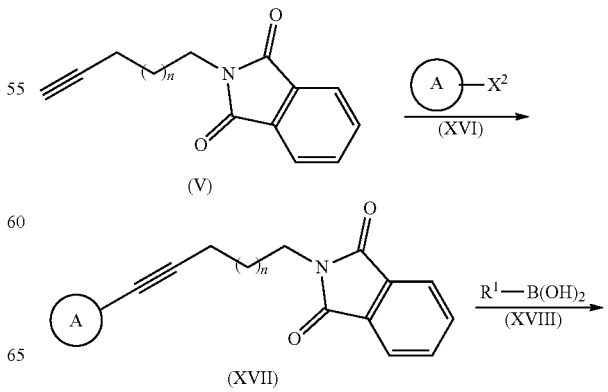

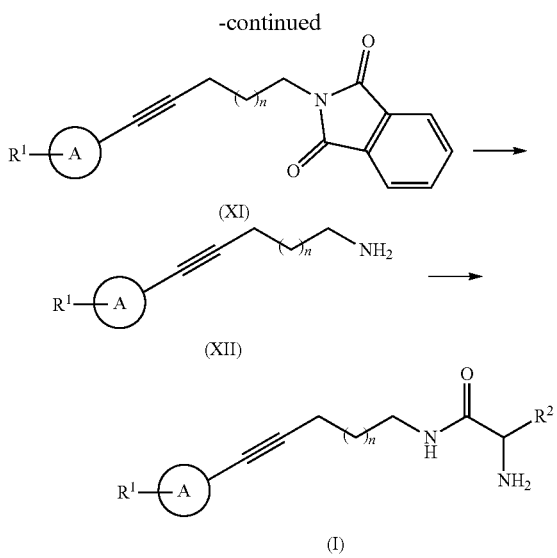

Accordingly, a suitably substituted compound of formula (V) is reacted with a suitably substituted compound of formula (XVI), wherein $X^2$ is a suitably selected leaving group such as bromo, iodo, triflate, and the like; in the presence of a suitably selected catalysts such as $Ph(PPh_3)_2Cl_2$, $Pd(OAc)_2Cl_2$, $Pd(dppp)Cl_2$, $Pd(dppf)Cl_2$, and the like; preferably in the presence of CuI; in the presence of a base such as TEA, DIPEA, pyridine, and the like; in the presence of a catalyst such as DMAP, and the like; in a suitably selected organic solvent such as DMF, NMP, and the like; at a temperature in the range of from about 50° C. to about 100° C., for example at about 70° C.; to yield the corresponding compound of formula (XVII).

The compound of formula (XVII) is reacted with a suitably substituted compound of formula (XVIII), a known compound or compound prepared by known methods; in the presence of a suitably selected coupling agent such as $Pd(PPh_3)_4$, $Pd(OAc_2)Cl_2$, $Pd(dppf)Cl_2$, and the like; in a suitably selected solvent or mixture thereof such as 1,4-dioxane, water, a mixture of THF and water, and the like; to yield the corresponding compound of formula (XI).

The compound of formula (XI) is reacted with hydrazine, a known compound; in a suitably selected alcohol such as methanol, ethanol, isopropanol, and the like, to yield the corresponding compound of formula (XII).

The compound of formula (XII) is further reacted, (for example, with a suitably substituted compound of formula (XIII), followed by de-protection), as described in Scheme 2 above; to yield the corresponding compound of formula (I).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1,000 mg or any amount or range therein, and may be given at a dosage of from about 0.01 mg/kg/day to about 100 mg/kg/day, or any amount or range therein, preferably from about 0.1 to about 50 mg/kg/day, or any amount or range therein, preferably from about 0.1 to about 25 mg/kg/day, or any amount or range therein, preferably from about 0.1 to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1,000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and about 1,000 mg of the compound, or any amount or range therein; preferably about 1.0 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by DPP-1 is required.

The daily dosage of the products may be varied over a wide range from 0.1 to about 10,000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250, 500 and 1,000 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any amount or range therein. Preferably, the range is from about 0.1 mg/kg to about 50.0 mg/kg of body weight per day, or any amount or range therein. More preferably, from about 0.1 mg/kg to about 25.0 mg/kg of body weight per day, or any amount or range therein. More preferably, from about 0.1 mg/kg to about 15.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. For example, Methot, N., et al., "In Vivo Inhibition of Serine Protease Processing Requires a High Fractional Inhibition of Cathepsin C", *Molecular Pharmacology*, (2008), Vol. 73, No. 6, pp 1857-1865 disclose an in vivo assay in rats for measuring inhibition of Cathepsin C (DPP-1).

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Compound #56

(S)-2-amino-N-(5-(4-(methylsulfonyl)phenyl)pent-4-ynyl)butanamide

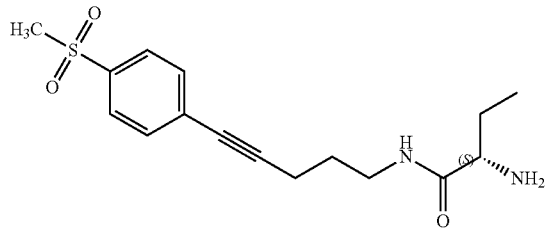

STEP A: Pent-4-yn-1-amine

A 1-L round bottom flask was charged with 2-(pent-4-ynyl)isoindoline-1,3-dione (25.3 g, 0.119 mol), ethanol (390 mL) and water (4.4 mL). Hydrazine (7.8 mL, 0.248 mol) was added and the resulting mixture was stirred at room temperature for 24 h. Water (90 mL) was added, the resulting mixture was acidified with 2N HCl to pH 3, and then stirred at room temperature for 30 minutes. The solid was filtered off, the filtrate was concentrated in vacuo. Water (90 mL) was added to the resulting residue and the resulting mixture was cooled using an ice/water bath. To the resulting mixture was then slowly added a 10 M NaOH solution (100 mL). The resulting mixture was stirred at room temperature for 15 minutes, and extracted with dichloromethane (2×600 mL). The organic layer was dried with sodium sulfate, filtered, and concentrated in vacuo to yield pent-4-yn-1-amine as an oil, which was used in the next step without further purification. $^1$H NMR (300 MHz, CDCl$_3$) δ 2.81 (t, J=6.8 Hz, 2H), 2.24-2.31 (m, 2H), 1.96 (s, 1H), and 1.62-1.71 (m, 2H).

STEP B: —(S)-(2,2,2-trifluoroacetylamino)-butyric acid

A 500 mL round bottom flask was charged with (S)-2-aminobutanoic acid (5.0 g, 0.048 mol) and dichloromethane (170 mL). The resulting mixture was cooled using an ice/water bath, trifluoroacetic anhydride (8.8 mL, 0.063 mol) was added slowly and the resulting mixture stirred at room temperature for 18 h. The resulting mixture was then concentrated in vauco to yield 2-(S)-(2,2,2-trifluoroacetylamino)-butyric acid as an oil, which was used in the next step without further purification.

STEP C: (S)—N-(pent-4-ynyl)-2-(2,2,2-trifluoroacetamido)butanamide

A 500 mL round bottom flask was charged with 2-(S)-(2,2,2-trifluoroacetylamino)-butyric acid (5.0 g, 0.025 mol), 1-hydroxybenzotriazole hydrate (4.5 g, 0.033 mol), N-(3-dimethylaminopropyl)-N'-ethylcarbodiimide hydrochloride (6.4 g, 0.033 mol), 4-(dimethylamino)pyridine (0.02 g, 0.163 mmol), and dimethylformamide (95 mL). To the resulting mixture was then added triethylamine (10.6 mL, 0.076 mol) and pent-4-yn-1-amine (2.7 g, 0.033 mol). The resulting mixture was stirred at room temperature for 22 h, then concentrated in vacuo and the resulting residue purified via flash silica gel chromatography (Analogix IF-280, SF65-400 g column, gradient 90:10-40:60 Heptane:EtOAc) to yield (S)—N-(pent-4-ynyl)-2-(2,2,2-trifluoroacetamido)butanamide.
$^1$H NMR (300 MHz, CDCl$_3$) δ 4.46-4.53 (m, 1H), 3.32-3.48 (m, 2H), 2.23-2.29 (m, 2H), 2.00 (s, 1H), 1.86-1.98 (m, 2H), 1.71-1.83 (m, 2H), and 0.91-0.98 (m, 3H).

STEP D: (S)-2-amino-N-(5-(4-(methylsulfonyl)phenyl)pent-4-ynyl) butanamide (S)—N-(pent-4-ynyl)-2-(2,2,2-trifluoroacetamido)butanamide (0.246 g, 0.93 mmol), 4-bromophenyl methyl sulfone (0.200 g, 0.85 mmol), triethylamine (5 ml), copper iodine (0.032 g, 0.17 mmol) and Pd(PPh$_3$)$_2$Cl$_2$ (0.175 g, 0.25 mmol) were combined in anhydrous DMF (5 ml) and heated to 70° C. in a sealed tube overnight. The resulting mixture was then concentrated in vacuo and ethyl acetate (46 ml) was added to the remaining residue. The resulting mixture was washed with 1N HCl (2×23 ml), water (23 ml), brine (23 ml), dried (MgSO$_4$) and concentrated in vacuo. The resulting residue was chromatographed eluting with ethyl acetate/heptanes (30:70) to yield a residue. The residue was dissolved in THF (0.5 ml)/MeOH (0.13 ml) and cooled to 0° C. 3N NaOH (0.10 ml, 0.30 mmol) was added, the resulting mixture was warmed to room temperature and stirred overnight. The resulting mixture was then diluted with water (0.25 ml) and concentrated in vacuo. The aqueous layer was extracted with methylene chloride (3×5 ml), dried (MgSO$_4$) and concentrated in vacuo. The resulting residue was chromatographed eluting with methylene chloride/methanol (95:5) followed by elution with methylene chloride/methanol/ammonium hydroxide (95:5:0.4) to yield (S)-2-amino-N-(5-(4-(methylsulfonyl)phenyl)pent-4-ynyl)butanamide. ES-MS m/z 323 (MH+).

Example 2

Compound #15

(S)-2-amino-4-hydroxy-N-(5-(3-(piperidin-4-yloxy)phenyl)pent-4-ynyl)butanamide

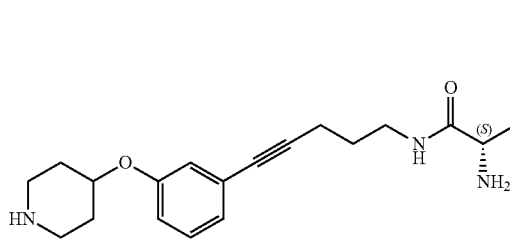

To a solution of N-Boc-L-Homoserine (16 mg, 0.075 mmol, 1.5 eq) and HOBT hydrate (12 mg, 0.085 mmol, 1.7 eq) in DMF (2 mL) was added PS-carbodiimide (also known as N-Cyclohexylcarbodiimide-N'-propoxymethyl polystyrene, purchased from Biotage) (80 mg, 1.25 mmol/g resin, 0.1 mmol, 2.0 eq). After 10 minutes, a solution of tert-butyl 4-(3-(5-aminopent-1-ynyl)phenoxy)piperidine-1-carboxylate (0.25 mL of a 0.2 M solution in DCM, 0.05 mmol, 1.0 eq) was added and the resulting solution stirred overnight. To the resulting solution was then added MP-carbonate resin (95 mg, 2.64 mmol/g resin, 0.25 mmols, 5 eq), the suspension stirred 2 hrs, filtered, the resin washed with DCM and the filtrate concentrated by rotovap. The residue was taken up in 20% TFA/DCM (2 mL) and stirred 1 hr, methanol (1 mL) was added, and the resulting solution concentrated by rotovap. The resulting residue was purified by HPLC to yield (S)-2-amino-4-hydroxy-N-(5-(3-(piperidin-4-yloxy)phenyl)pent-4-ynyl)butanamide as a gum. ESI-MS (m/z): Calculated for $C_{20}H_{29}N_3O_3$: 360.2 (M+1); Measured: 360.2.

The following compounds were similarly prepared according to the procedure as described in Example 2 above, selecting and substituting suitably substituted reagents as would be recognized by one of ordinary skill in the art.

Example 3

Compound #16

(S)-2-amino-3-methyl-N-(5-(3-(piperidin-4-yloxy)phenyl)pent-4-ynyl)butanamide

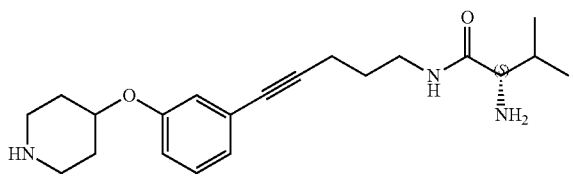

ESI-MS (m/z): Calculated for $C_{21}H_{31}N_3O_2$: 358.2 (M+1); Measured: 358.3.

Example 4

Compound #18

(S)-2-amino-N-(5-(3-(piperidin-4-yloxy)phenyl)pent-4-ynyl)pentanamide

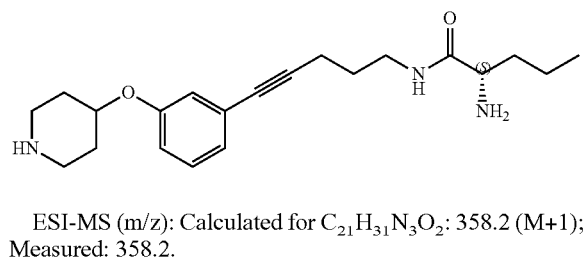

ESI-MS (m/z): Calculated for $C_{21}H_{31}N_3O_2$: 358.2 (M+1); Measured: 358.2.

Example 5

Compound #19

(S)-2-amino-N-(5-(3-(piperidin-4-yloxy)phenyl)pent-4-ynyl)-3-(1H-pyrazol-1-yl)propanamide

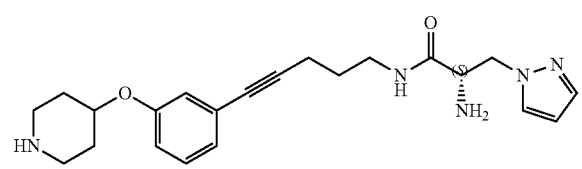

ESI-MS (m/z): Calculated for $C_{22}H_{29}N_5O_2$: 396.2 (M+1); Measured: 396.2.

Example 6

Compound #3

(S)-2-amino-N-(5-(3-(piperidin-4-yloxy)phenyl)pent-4-ynyl)pent-4-ynamide

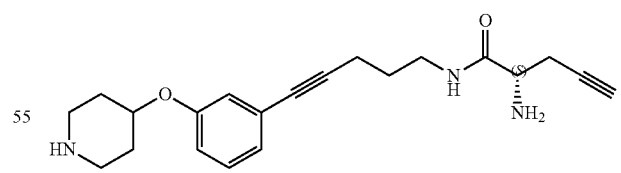

STEP A: 1-(4,4-dimethylpent-1-en-2-yl)-4-(3-iodophenoxy)piperidine

To a stirring solution of 3-iodophenol (9.65 g, 43.9 mmol), 1-Boc-4-hydroxypiperidine (8.83 g, 43.9 mmol), triphenylphosphine (12.65 g, 48.2 mmol) in THF (100 ml) at room temperature and DIAD (11.53 g, 57 mmol) were added. The resulting solution was stirred at room temperature overnight, then concentrated. The residue was dissolved in diethyl ether (200 ml). Heptane (100 ml) was added. The resulting precipitate was removed by filtration, the filtrate was concentrated and the resulting residue purified over silica gel column eluted with ethyl acetate/heptanes from 0/100 to 5/95 to yield 1-(4,4-dimethylpent-1-en-2-yl)-4-(3-iodophenoxy)piperidine as a colorless oil. M+Na$^+$=426.1.

STEP B: tert-Butyl 4-(3-(5-(1,3-dioxoisoindolin-2-yl)pent-1-ynyl)phenoxy)piperidine-1-carboxylate To a stirring solution of 1-(4,4-dimethylpent-1-en-2-yl)-4-(3-iodophenoxy)piperidine (15.61 g, 38.7 mmol), 2-(pent-4-ynyl)isoindoline-1,3-dione (9.08 g, 42.6 mmol), CuI (1.47 g, 7.7 mmol) in a mixture of DMF (100 ml) and triethyl amine (100 ml) at room temperature was added bis(triphenylphosphine)palladium (II) dichloride (8.15 g, 11.6 mmol). The resulting solution was stirred at room temperature overnight, then concentrated. The resulting residue was dissolved in ethyl acetate (300 ml), the resulting solution was extracted with hydrochloric acid (1 N) twice, water once, brine once, then dried over magnesium sulfate. The resulting solution was filtered and concentrated. The residue was purified over silica gel column eluted with ethyl acetate/heptanes from 30/70 to 40/60 to yield tert-butyl 4-(3-(5-(1,3-dioxoisoindolin-2-yl)pent-1-ynyl)phenoxy)piperidine-1-carboxylate as a deep colored oil. MH+ 489.36

STEP C: tert-butyl 4-(3-(5-aminopent-1-ynyl)phenoxy)piperidine-1-carboxylate

To a solution of tert-butyl 4-(3-(5-(1,3-dioxoisoindolin-2-yl)pent-1-ynyl)phenoxy)piperidine-1-carboxylate (10.65 g, 21.8 mmol) in ethanol (100 ml) was added hydrazine (2.1 g, 65.4 mmol). The resulting solution was heated under reflux for two hours, then cooled to room temperature, filtered and concentrated. The residue was dissolved in ethyl acetate (200 ml). The resulting solution was extracted with water twice, brine once, then dried over magnesium sulfate. The resulting solution was filtered and concentrated to yield tert-butyl 4-(3-(5-aminopent-1-ynyl)phenoxy)piperidine-1-carboxylate as a brown oil. MH+ 359.33

STEP D: (S)-tert-butyl 4-(3-(5-(2-(tert-butoxycarbonylamino)pent-4-ynamido)pent-1-ynyl)phenoxy)piperidine-1-carboxylate To a stirring solution of tert-butyl 4-(3-(5-aminopent-1-ynyl)phenoxy)piperidine-1-carboxylate (0.59 g, 1.6 mmol), Boc-L-propargylglycine (0.35 g, 1.6 mmol), N-ethyldiisopropylamine (0.73 ml, 4.1 mmol) in DMF (20 ml) was added HBTU (0.81 g, 2.1 mmol). The resulting solution was stirred at room temperature overnight. (S)-tert-Butyl 4-(3-(5-(2-(tert-butoxycarbonylamino)pent-4-ynamido)pent-1-ynyl)phenoxy)piperidine-1-carboxylate was isolated and purified over Gilson HPLC as a colorless oil. MH+ 554.44

STEP E: (S)-2-amino-N-(5-(3-(piperidin-4-yloxy)phenyl)pent-4-ynyl)pent-4-ynamide To a stirring solution of (S)-tert-butyl 4-(3-(5-(2-(tert-butoxycarbonylamino)pent-4-ynamido)pent-1-ynyl)phenoxy)piperidine-1-carboxylate (0.26 g, 0.47 mmol) in dichloromethane (4.0 ml), TFA (1.0 ml) was added. The resulting solution was stirred at room temperature for 1 hr, then concentrated. The resulting residue was purified over Gilson HPLC to yield the title compound as its corresponding TFA salt, as a white solid. MH+ 354.31

Examples 7-19

The following compounds were similarly prepared according to the procedure as described in Example 6 above, selecting and substituting a suitably substituted acid for the Boc-L-propargylglycine reagent in STEP D, as would be recognized by one of ordinary skill in the art.

| Example No. | ID No. | MH+ |
|---|---|---|
| 7 | 1 | 406.32 |
| 8 | 3 | 354.31 |
| 9 | 8 | 370.35 |
| 10 | 9 | 344.34 |
| 11 | 11 | 370.36 |
| 12 | 12 | 372.35 |
| 13 | 13 | 373.37 |
| 14 | 20 | 396.33 |
| 15 | 25 | 346.30 |
| 16 | 31 | 372.36 |
| 17 | 33 | 407.35 |
| 18 | 63 | 412.21 |
| 19 | 90 | 407.27 |

Example 20

Compound #79

(S)-2-amino-N-(5-(3-((R)-piperidin-3-yloxy)phenyl)pent-4-ynyl)pent-4-ynamide

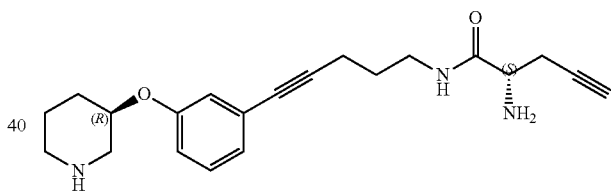

STEP A: (R)-tert-butyl 3-(3-iodophenoxy)piperidine-1-carboxylate

Following the procedure as described in Example 6, STEP A, substituting (S)-tert-butyl 3-hydroxypiperidine-1-carboxylate for 1-Boc-4-hydroxypiperidine, (R)-tert-butyl 3-(3-iodophenoxy)piperidine-1-carboxylate was prepared as a colorless oil. MH+ 404.11.

STEP B: (R)-tert-butyl 3-(3-iodophenoxy)piperidine-1-carboxylate

Following the procedure as described in Example 6, STEP B, substituting (R)-tert-butyl 3-(3-iodophenoxy)piperidine-1-carboxylate for 1-(4,4-dimethylpent-1-en-2-yl)-4-(3-iodophenoxy)piperidine, (R)-tert-butyl 3-(3-iodophenoxy)piperidine-1-carboxylate was prepared as a colorless oil. MH+ 489.27.

STEP C: (R)-tert-butyl 3-(3-iodophenoxy)piperidine-1-carboxylate

Following the procedure as described in Example 6, STEP C, substituting (R)-tert-butyl 3-(3-iodophenoxy)piperidine- 1-carboxylate for tert-butyl 4-(3-(5-(1,3-dioxoisoindolin-2-yl)pent-1-ynyl)phenoxy)piperidine-1-carboxylate, (R)-tert-butyl 3-(3-iodophenoxy)piperidine-1-carboxylate was prepared as a black oil. MH+ 359.27.

STEP D: (R)-2-amino-N-(5-(3-((S)-piperidin-3-yloxy)phenyl)pent-4-ynyl)pent-4-ynamide Following the procedure as described in Example 6, STEPS D and E, substituting (R)-tert-butyl 3-(3-iodophenoxy)piperidine-1-carboxylate for tert-butyl 4-(3-(5-aminopent-1-ynyl)phenoxy)piperidine-1-carboxylate, the title compound was prepared as its corresponding TFA salt, as a black solid. MH+ 354.25

Example 21

Compound #78

(S)-2-amino-N-(5-(3-((R)-piperidin-3-yloxy)phenyl)pent-4-ynyl)butanamide

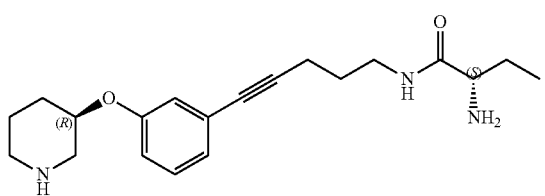

Following the procedure as described in Example 20, STEP D substituting (S)-2-(tert-butoxycarbonylamino)butanoic acid for Boc-L-propargylglycine, the title compound was prepared as its corresponding TFA salt. MH+ 344.27

Example 22

Compound #85

(S)-2-amino-N-(5-(3-((S)-piperidin-3-yloxy)phenyl)pent-4-ynyl)pent-4-ynamide

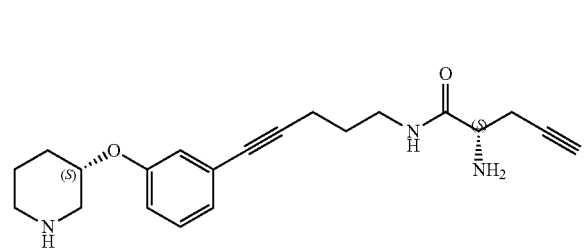

STEP A: (S)-tert-butyl 3-(3-iodophenoxy)piperidine-1-carboxylate

Following the procedure as described in Example 6, STEP A, substituting (R)-tert-butyl 3-hydroxypiperidine-1-carboxylate for 1-Boc-4-hydroxypiperidine, (S)-tert-butyl 3-(3-iodophenoxy)piperidine-1-carboxylate was prepared as colorless oil. MH+ 404.09.

STEP B: (S)-tert-butyl 3-(3-(5-(1,3-dioxoisoindolin-2-yl)pent-1-ynyl)phenoxy)piperidine-1-carboxylate Following the procedure as described in Example 6, STEP B, substituting (S)-tert-butyl 3-(3-iodophenoxy)piperidine-1-carboxylate for 1-(4,4-dimethylpent-1-en-2-yl)-4-(3-iodophenoxy)piperidine, (S)-tert-butyl 3-(3-(5-(1,3-dioxoisoindolin-2-yl)pent-1-ynyl)phenoxy)piperidine-1-carboxylate was prepared as a colorless oil. MH+ 489.27.

STEP C: (S)-tert-butyl 3-(3-(5-aminopent-1-ynyl)phenoxy)piperidine-1-carboxylate Following the procedure as described in Example 6, STEP C, substituting (S)-tert-butyl 3-(3-(5-(1,3-dioxoisoindolin-2-yl)pent-1-ynyl)phenoxy)piperidine-1-carboxylate for tert-butyl 4-(3-(5-(1,3-dioxoisoindolin-2-yl)pent-1-ynyl)phenoxy)piperidine-1-carboxylate, (S)-tert-butyl 3-(3-(5-aminopent-1-ynyl)phenoxy)piperidine-1-carboxylate was prepared as a black oil. MH+ 359.26.

STEP D: (S)-2-amino-N-(5-(3-((S)-piperidin-3-yloxy)phenyl)pent-4-ynyl)pent-4-ynamide Following the procedure a described in Example 6, STEP D and E, substituting (S)-tert-butyl 3-(3-(5-aminopent-1-ynyl)phenoxy)piperidine-1-carboxylate for tert-butyl 4-(3-(5-aminopent-1-ynyl)phenoxy)piperidine-1-carboxylate, the title compound was obtained as TFA salt, as a black solid. MH+ 354.25

Example 23

Compound #80

(S)-2-amino-N-(5-(3-((S)-piperidin-3-yloxy)phenyl)pent-4-ynyl)butanamide

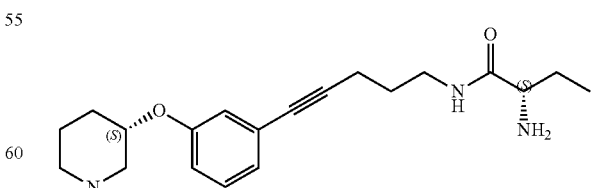

Following the procedure as described in Example 22, STEP D, substituting (S)-2-(tert-butoxy-carbonyl-amino)butanoic acid for Boc-L-propargylglycine, the title compound was prepared as its corresponding TFA salt. MH+ 344.27

Example 24

Compound #6

(S)-2-amino-N-(4-(3-(piperidin-4-yloxy)phenyl)but-3-ynyl)pent-4-ynamide

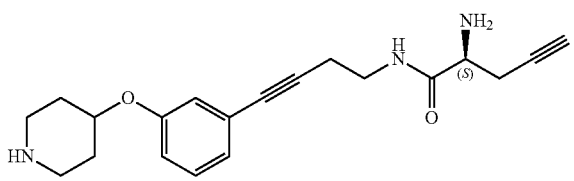

STEP A: tert-butyl 4-(3-(4-(1,3-dioxoisoindolin-2-yl)but-1-ynyl)phenoxy)piperidine-1-carboxylate Following the procedure as described in Example 6, STEP B, substituting 2-(but-3-ynyl)isoindoline-1,3-dione for 2-(pent-4-ynyl)isoindoline-1,3-dione, tert-butyl 4-(3-(4-(1,3-dioxoisoindolin-2-yl)but-1-ynyl)phenoxy)piperidine-1-carboxylate was prepared as a deep colored oil. MH+ 475.3.

STEP B: tert-butyl 4-(3-(4-aminobut-1-ynyl)phenoxy)piperidine-1-carboxylate

Following the procedure as described in Example 6, STEP C, substituting tert-butyl 4-(3-(4-(1,3-dioxoisoindolin-2-yl)but-1-ynyl)phenoxy)piperidine-1-carboxylate for tert-butyl 4-(3-(5-(1,3-dioxoisoindolin-2-yl)pent-1-ynyl)phenoxy)piperidine-1-carboxylate, tert-butyl 4-(3-(4-aminobut-1-ynyl)phenoxy)piperidine-1-carboxylate was prepared as a colorless oil. MH+ 345.32

STEP C: (S)-2-amino-N-(4-(3-(piperidin-4-yloxy)phenyl)but-3-ynyl)pent-4-ynamide

Following the procedure as described in Example 6, STEPS D and E, substituting tert-butyl 4-(3-(4-aminobut-1-ynyl)phenoxy)piperidine-1-carboxylate for tert-butyl 4-(3-(5-aminopent-1-ynyl)phenoxy)piperidine-1-carboxylate, the title compound was prepared as its corresponding TFA salt, as a white solid. MH+ 340.32

Example 25

Compound #24

(S)-2-amino-N-(4-(3-(piperidin-4-yloxy)phenyl)but-3-ynyl)pent-4-ynamide

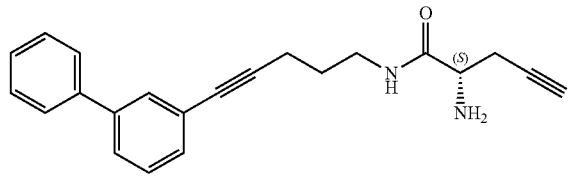

STEP A: 2-(5-(3-bromophenyl)pent-4-ynyl)isoindoline-1,3-dione

1-Bromo-3-fluoro-benzene (1.0 mL, 7.8 mmol), 2-pent-4-ynyl-isoindole-1,3-dione (1.8 g, 8.6 mmol), Pd(PPh$_3$)$_2$Cl$_2$ (191 mg, 0.27 mmol), CuI (118 mg, 0.62 mmol), and triethylamine (4.4 mL, 31.3 mmol) were taken up into DMF (10 mL) and stirred at room temperature for four hours. The reaction was then quenched with saturated NaHCO$_3$ and the resulting mixture extracted with EtOAc and washed with brine, then dried over sodium sulfate and the solvent removed in vacuo. The resulting residue was purified on normal phase chromatography (Heptane/EtOAc) to yield 2-(5-(3-bromophenyl)pent-4-ynyl)isoindoline-1,3-dione. MH+ 368, 370

STEP B: 2-(Biphenyl-3-yl)pent-4-ynyl)isoindoline-1,3-dione 2-(5-(3-Bromophenyl)pent-4-ynyl)isoindoline-1,3-dione (0.31 g, 0.84 mmol), phenyl boronic acid (206 mg, 1.68 mmol), and Pd (PPh$_3$)$_4$ (0.23, 0.2 mmol) were taken into DME (5 mL) and stirred at 80° C. for two hours. The reaction was then quenched with saturated NaHCO$_3$ and the resulting mixture extracted with EtOAc, washed with brine, then dried over sodium sulfate and the solvent removed in vacuo. The resulting residue was purified on normal phase chromatography (Heptane/EtOAc) to yield 2-(5-(biphenyl-3-yl)pent-4-ynyl)isoindoline-1,3-dione. MH+ 366.3

STEP C: 5-(Biphenyl-3-yl)pent-4-yn-1-amine 2-(5-(Biphenyl-3-yl)pent-4-ynyl)isoindoline-1,3-dione (0.11 g, 0.30 mmol) and hydrazine monohydrate (0.030 mL, 0.60 mmol) were taken up into ethanol (3 mL) and stirred at 80° C. for 2.5 hours. The resulting mixture was filtered and the solvent removed in vacuo to yield 5-(biphenyl-3-yl)pent-4-yn-1-amine, which was used in the next step without further purification. MH+ 236.2

STEP D: (S)-2-amino-N-(4-(3-(piperidin-4-yloxy)phenyl)but-3-ynyl)pent-4-ynamide 5-(Biphenyl-3-yl)pent-4-yn-1-amine (0.040 g, 0.17 mmol), 2-tert-Butoxycarbonylamino-pent-4-ynoic acid (40 mg, 0.19 mmol), HOBt (28 mg, 0.21 mmol), EDCl (40 mg, 0.21 mmol), and DIEA (0.044 mL, 0.25 mmol) were taken into DMF (3 mL) and stirred at room temperature overnight. The reaction was then quenched with water and the resulting mixture extracted with EtOAc. The organic layer was washed with saturated NaHCO$_3$ and brine, then dried over sodium sulfate and the solvent removed in vacuo. The resulting residue was taken up into DCM/TFA (4/1, 5 mL) and the resulting mixture was stirred at room temp for 1 hr. The solvent was removed in vacuo and prepped on the Gilson HPLC to yield the title compound, as its corresponding TFA salt. MH+ 331.2; $^1$H NMR (300 MHz, DMSO): δ 1.6-1.8 (m, 3H), 2.45 (m, 2H), 2.7 (s, 2H), 3.2-3.4 (m, 2H), 3.9 (s, 1H), 7.3-7.4 (m, 5H), 7.6-7.7 (m, 4H), 8.3 (s, 2H), 8.6 (s, 1H)

Example 26

Compound #7

(S)-2-amino-N-(5-(3-methoxy-5-(piperidin-4-yloxy)phenyl)pent-4-ynyl)pent-4-ynamide

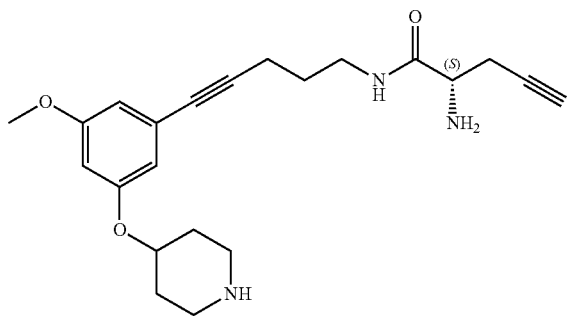

STEP A: 3-Bromo-5-methoxyphenol

1-Bromo-3,5-dimethoxy-benzene (0.217 g, 0.001 mol) and KCN (0.20 g, 0.003 mol) were taken up into DMSO (10 mL) and the resulting mixture stirred at 120° C. for six hours, then at 150° C. overnight. The mixture was maintained at this temperature, with stirring for another day. The reaction was then quenched with water and the resulting mixture extracted with EtOAc. The organic layer was washed with saturated NaHCO$_3$, brine, then dried over sodium sulfate and the solvent removed in vacuo. The resulting residue was purified on normal phase chromatography (Heptane/EtOAc) to yield 3-bromo-5-methoxyphenol. MH$^+$ 203, 205

STEP B: tert-Butyl 4-(3-bromo-5-methoxyphenoxy)piperidine-1-carboxylate

3-Bromo-5-methoxyphenol (0.18 g, 0.89 mmol) and triphenylphosphine (0.284, 1.07 mmol) were taken into THF (5 mL) and the resulting mixture cooled to 0° C. 4-Hydroxy-piperidine-1-carboxylic acid tert-butyl ester (0.18 g, 0.89 mmol), and DIAD (0.207 mL, 1.07 mmol) were taken up into THF (5 mL) and added slowly to the mixture, which was then stirred at room temperature over night. The resulting mixture was taken into EtOAc and washed with saturated NaHCO$_3$ and brine. The solvent was dried over sodium sulfate and removed in vacuo. The resulting residue was purified on normal phase chromatography (EtOAc/heptane) to yield tert-butyl 4-(3-bromo-5-methoxyphenoxy)piperidine-1-carboxylate. MH$^+$ 386.2, 388.2

STEP C: tert-Butyl 4-(3-(5-(1,3-dioxoisoindolin-2-yl)pent-1-ynyl)-5-methoxyphenoxy)piperidine-1-carboxylate tert-Butyl 4-(3-bromo-5-methoxyphenoxy)piperidine-1-carboxylate (0.90 g, 2.3 mmol), 2-pent-4-ynyl-isoindole-1,3-dione (0.75 g, 3.45 mmol), Pd(PPh$_3$)$_4$ (0.27 g, 0.23 mmol), CuI (45 mg, 0.23 mmol) and TEA (1 mL) were taken into DMF (2 mL) and the resulting mixture stirred at 80° C. for six hours. The reaction was quenched with water and the resulting mixture extracted with ethyl acetate. The organic layer was washed with brine. The solvent was dried over sodium sulfate and removed in vacuo. The resulting residue was purified on normal phase chromatography (EtOAc/heptane) to yield tert-butyl 44345-(1,3-dioxoisoindolin-2-yl)pent-1-ynyl)-5-methoxyphenoxy)piperidine-1-carboxylate. MH$^+$ 519.2

STEP D: tert-Butyl 4-(3-(5-aminopent-1-ynyl)-5-methoxyphenoxy)piperidine-1-carboxylate tert-Butyl 4-(3-(5-(1,3-dioxoisoindolin-2-yl)pent-1-ynyl)-5-methoxyphenoxy)piperidine-1-carboxylate (0.500 g, 0.97 mmol) and hydrazine monohydrate (0.094 mL, 1.94 mmol) were taken up into ethanol (5 mL) and the resulting mixture was stirred at 80° C. for 2.5 hours. The resulting mixture was filtered and the solvent was removed in vacuo to yield tert-butyl 4-(3-(5-aminopent-1-ynyl)-5-methoxyphenoxy)piperidine-1-carboxylate. MH$^+$ 388.2

STEP E: (S)-2-amino-N-(5-(3-methoxy-5-(piperidin-4-yloxy)phenyl)pent-4-ynyl)pent-4-ynamide tert-Butyl 4-(3-(5-aminopent-1-ynyl)-5-methoxyphenoxy)piperidine-1-carboxylate (0.33 g, 0.85 mmol), 2-tert-butoxycarbonylamino-pent-4-ynoic acid (181 mg, 0.85 mmol), HOBt (138 mg, 1.02 mmol), EDCl (195 mg, 1.02 mmol), and DIEA (0.22 mL, 1.28 mmol) were taken into DMF (5 mL) and stirred at room temperature overnight. The reaction was quenched with water and the resulting mixture extracted with EtOAc. The organic layer was washed with saturated NaHCO$_3$ and brine, then dried over sodium sulfate and the solvent removed in vacuo. The resulting residue was taken up into DCM/TFA (4/1, 5 mL) and the resulting mixture stirred at room temp for 1 hr. The solvent was removed in vacuo and the resulting residue prepped on the Gilson HPLC to yield (S)-2-amino-N-(5-(3-methoxy-5-(piperidin-4-yloxy)phenyl)pent-4-ynyl)pent-4-ynamide as its corresponding TFA salt. MH$^+$ 384.3; $^1$H NMR (300 MHz, DMSO): δ 1.6-1.8 (m, 4H), 2.1 (m, 2H), 2.4-2.6 (m, 4H), 2.7 (s, 2H), 2.9-3.4 (m, 6H), 3.6 (s, 3H), 3.985 (m, 1H), 4.65 (m, 1H), 6.5 (d, 2H), 6.6 (s, 1H), 8.3 (s, 2H), 8.5-8.7 (m, 1H).

Example 27

Compound #63

(S)-2-amino-N-(5-(3-(piperidin-4-yloxy)phenyl)pent-4-ynyl)-3-(thiophen-2-yl)propanamide

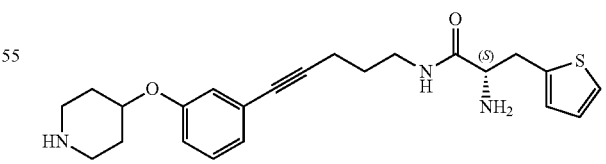

To a stirring solution of tert-butyl 4-(3-(5-aminopent-1-ynyl)phenoxy)piperidine-1-carboxylate (0.22 g, 0.61 mmol), boc-L-propargylglycine (0.35 g, 1.6 mmol), N-ethyldiisopropylamine (0.73 ml, 4.1 mmol) in DMF (20 ml) was added HBTU (0.81 g, 2.1 mmol). The resulting solution was stirred at room temperature overnight. (S)-tert-Butyl 4-(3-(5-(2-(tert-butoxycarbonylamino)-3-(thiophen-2-yl)propanamido)

pent-1-ynyl)phenoxy)piperidine-1-carboxylate was isolated as a residue and purified over Gilson HPLC.

To a stirring solution of the purified (S)-tert-butyl 4-(3-(5-(2-(tert-butoxycarbonylamino)-3-(thiophen-2-yl)propanamido)pent-1-ynyl)phenoxy)piperidine-1-carboxylate (0.26 g, 0.47 mmol) in dichloromethane (1.6 ml) was added TFA (0.4 ml) and the resulting mixture was stirred at room temperature for 1 hr. The resulting solution was concentrated and the residue purified over Gilson HPLC to yield (S)-2-amino-N-(5-(3-(piperidin-4-yloxy)phenyl)pent-4-ynyl)-3-(thiophen-2-yl)propanamide as its corresponding TFA salt, as a deep colored oil. MH+ 412.25. $^1$H NMR (300 MHz, DMSO), δ: 8.50 (1H, d), 8.23 (1H, s), 7.43 (1H, d), 7.30 (1H, m), 6.90 (3H, m), 4.65 (1H, m), 3.96 (1H, m), 2.96-3.30 (8H, m), 2.35 (2H, m), 2.10 (2H, m), 1.60-1.80 (4H, m)

Additional compounds of the present invention were similarly prepared according to the procedures as described in the Schemes and Examples outlined herein, selecting and substituting suitably substituted reagents, as would be readily recognized by one of ordinary skill in the art.

Biological Example 1

DPP-1 Inhibition Assay (In Vitro)

Test compounds were assessed for DPP-1 (Cathepsin C) inhibitory activity using a fluorogenic substrate, GR-AMC (Glycine-Arginine-amino-4-methylcoumarin, Bachem, I-1215). The amount of amino-methylcoumarin released is proportional to the DPP-1 activity, and the reaction is monitored kinetically with a Molecular Devices plate reader using black 96-well plates.

All compounds were tested under room temperature conditions. The assay buffer consisted of 50 mM HEPES, pH 7.0, 100 mM NaCl, 2 mM glutathione (GSH), and 0.002% TWEEN 20. GSH and TWEEN 20 were added to the buffer fresh daily. Just prior to use, an in-house preparation of recombinant human DPP-1 (240 μM stock, MW 49.6 kD) was diluted 600-fold in assay buffer containing fresh 2 mM dithiothreitol (DTT) to activate the enzyme, then diluted into assay buffer (without DTT) 133-fold for a DPP-1 working solution of 3 nM. Test compounds were diluted in DMSO for 20× their final assay concentrations.

Additions to a 96-well black Costar 3915 plates were as follows: 90 μL of 11 μM GR-AMC, 5 μL test compound (followed by mixing), and 5 μL 3 nM DPP1 to start the reaction. Fluorescent reactions were monitored kinetically at 360 nm excitation, 440 nm emission on a Molecular Devices Spectramax XPS reader. The Softmax Pro software of the reader determined the initial velocity of the selected data (the first 3-5 minutes of the reaction), and the best linear regression fit of the initial kinetic data. Final assay conditions were 0.15 nM DPP-1, 10 uM GR-AMC, 50 mM HEPES, pH 7.0, 100 mM NaCl, 2 mM GSH, 0.002% TWEEN 20, 1 uM DTT, 5.0% DMSO. Initial velocity rates were plotted vs. test compound concentration by use of a four-parameter logistics equation (nonlinear regression, sigmoidal dose-response (variable slope), with fixed Hill (1.0) using GraphPad Prism® software for determination of DPP-1 $IC_{50}$. Within-run assay coefficient of variation (CV) was generally <10%; between-run CV <20%.

Representative compounds of the present invention were tested according to the procedure as described above, with results as listed in Table 2, below. Where a compound was tested according to the above procedure multiple times, the average value is listed in the Table below. Additionally, Table 2 below lists the measured mass for said representative compounds of the present invention, more particularly the mass of the MH+ ion.

TABLE 2

| ID No | $IC_{50}$ (μM) | MH+ |
|---|---|---|
| 1 | 15.3 | 403 |
| 3 | 0.39 | 354 |
| 6 | 2.43 | 340 |
| 7 | 1.60 | 384 |
| 8 | 1.64 | 370 |
| 9 | 1.37 | 344 |
| 11 | 15.26 | 370 |
| 12 | 5.92 | 372 |
| 13 | 97.99 | 373 |
| 15 | 2.50 | 360 |
| 16 | 12.8 | 357 |
| 18 | 1.70 | 358 |
| 19 | 9.10 | 396 |
| 20 | 0.52 | 396 |
| 24 | 0.40 | 331 |
| 25 | 10.00 | 346 |
| 31 | 30.00 | 372 |
| 33 | 15.0 | 407 |
| 35 | 5.80 | 275 |
| 39 | 0.35 | 281 |
| 40 | 0.214 | 275 |
| 41 | 2.53 | 295 |
| 49 | 3.28 | 273 |
| 51 | 15.0 | 289 |
| 55 | 9.50 | 287 |
| 56 | 18.00 | 323 |
| 57 | 17.00 | 305 |
| 58 | 11.00 | 313 |
| 59 | 12.00 | 305 |
| 60 | 6.00 | 301 |
| 61 | 6.80 | 321 |
| 63 | 0.15 | 412 |
| 71 | >100[a] | 344 |
| 72 | 10.00 | 313 |
| 73 | 15.00 | 295 |
| 74 | 26.00 | 313 |
| 75 | 39.00 | 327 |
| 76 | 14.00 | 301 |
| 77 | 33.00 | 273 |
| 78 | 3.90 | 344 |
| 79 | 2.90 | 354 |
| 80 | 2.30 | 354 |
| 81 | 5.60 | 321 |
| 82 | 17.00 | 296 |
| 83 | 8.50 | 309 |
| 84 | 7.20 | 313 |
| 85 | 1.20 | 344 |
| 86 | 2.40 | 351 |
| 87 | 13.00 | 325 |
| 88 | 23.00 | 339 |
| 89 | 7.90 | 296 |
| 90 | 12.00 | 407 |
| 91 | 10.00 | 285 |
| 92 | 17.0 | 275 |
| 95 | 1.20 | 287 |
| 96 | 2.70 | 281 |
| 97 | 5.00 | 303 |
| 98 | 7.90 | 245 |
| 99 | 12.00 | 275 |
| 100 | 6.30 | 302 |
| 101 | 1.70 | 333 |
| 102 | 6.10 | 281 |
| 103 | 5.40 | 302 |
| 104 | 8.00 | 261 |
| 105 | >10[b] | 311 |
| 106 | 6.00 | 313 |

[a] For this compound, the number of different concentrations tested was not sufficient to calculate an $IC_{50}$ value beyond a determination that it was greater than about 100 μM.
[b] For this compound, the number of different concentrations tested was not sufficient to calculate an $IC_{50}$ value beyond a determination that it was greater than about 10 μM.

Solid Oral Dosage Formulation

Prophetic Example

As a specific embodiment of an oral composition, 100 mg of the Compound #63 prepared as in Example 27 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:

1. A compound of formula (I)

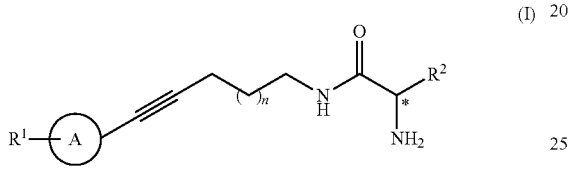

wherein

R$^1$ is selected from the group consisting of hydrogen, C$_{3-8}$cycloalkyl, phenyl, benzyloxy- and piperidinyl-oxy-;

is a ring structure selected from the group consisting of phenyl, naphthyl, fluorenyl, isoquinolinyl, benzofuryl, benzothiophenyl, benzo[1,3]dioxolyl and 2,3-dihydro-benzo[1,4]dioxinyl;

wherein the

ring structure is optionally substituted with one or more substituents independently selected from the group consisting of halogen, hydroxy, C$_{1-4}$alkyl, halogenated C$_{1-4}$alkyl, C$_{1-4}$alkoxy, halogenated C$_{1-4}$alkoxy, (C$_{1-4}$alkoxy)-(C$_{1-4}$alkyl)-, (C$_{1-4}$-alkyl)-SO$_2$— and (C$_{1-4}$alkyl)-C(O)—NH—;

n is an integer selected from 0 and 1;

R$^2$ is selected from the group consisting of C$_{1-4}$-alkyl, C$_{2-4}$alkenyl, C$_{2-4}$alkynyl, hydroxy substituted C$_{1-4}$-alkyl, NR$^A$R$^B$—(C$_{1-2}$alkyl)-, cyclopropyl-methyl-, benzyl- and heteroaryl-(CH$_2$)$_{1-2}$; wherein R$^A$ and R$^B$ are each independently selected from hydrogen or C$_{1-4}$-alkyl;

provided that R$^2$ is other than t-butyl;

or a pharmaceutically acceptable salt thereof.

2. A compound as in claim 1, wherein

R$^1$ is selected from the group consisting of hydrogen, C$_{5-6}$cycloalkyl, phenyl, benzyl-oxy- and piperidinyl-oxy-;

is a ring structure selected from the group consisting of phenyl, naphthyl, fluorenyl, isoquinolinyl, benzofuryl, benzothiophenyl, benzo[1,3]dioxolyl and 2,3-dihydro-benzo[1,4]dioxinyl;

wherein the

ring structure is optionally substituted with one to four substituents independently selected from the group consisting of halogen, hydroxy, C$_{1-4}$-alkyl, fluorinated C$_{1-4}$alkyl, C$_{1-4}$-alkoxy, (C$_{1-4}$-alkoxy)-(C$_{1-4}$alkyl)-, (C$_{1-4}$-alkyl)-SO$_2$— and (C$_{1-4}$-alkyl)-C(O)—NH—;

n is an integer selected from 0 and 1;

R$^2$ is selected from the group consisting of C$_{1-4}$-alkyl, C$_{2-4}$alkenyl, C$_{2-4}$alkynyl, hydroxy substituted C$_{2-4}$alkyl, NR$^A$R$^B$—(C$_{1-2}$alkyl)-, cyclopropyl-methyl-, benzyl- and heteroaryl-(C$_{1-4}$alkyl)-; wherein the heteroaryl is selected from the group consisting of pyridyl, pyrazolyl, imidazolyl and thienyl; and wherein R$^A$ and R$^B$ are each independently selected from hydrogen or C$_{1-2}$alkyl;

provided that R$^2$ is other than t-butyl;

or a pharmaceutically acceptable salt thereof.

3. A compound as in claim 2, wherein

R$^1$ is selected from the group consisting of hydrogen, C$_{5-6}$cycloalkyl, phenyl, benzyl-oxy, piperidin-4-yl-oxy and piperidin-3-yl-oxy; wherein the R$^1$ group is bound to the

ring at the 2-, 3- or 4-position;

is a ring structure selected from the group consisting of phenyl, naphthyl, 9H-fluorenyl, isoquinolinyl, benzofuryl, benzothiophenyl, benzo[1,3]dioxolyl and 2,3,-dihydro-benzo[1,4]dioxinyl;

wherein the phenyl or naphth-1-yl is optionally substituted with one to four substituent independently selected from the group consisting of hydroxy, halogen, C$_{1-4}$-alkyl, C$_{1-2}$alkoxy, trifluoromethyl, (C$_{1-2}$alkoxy)-(C$_{1-2}$-alkyl)-, C$_{1-2}$alkyl-SO$_2$— and C$_{1-2}$alkyl-C(O)—NH—;

n is an integer selected from 0 and 1;

R$^2$ is selected from the group consisting of C$_{1-4}$-alkyl, hydroxy substituted C$_{1-2}$alkyl, C$_{2-4}$alkenyl, C$_{2-4}$alkynyl, NH$_2$—(C$_{1-2}$alkyl)-, cyclopropyl-methyl-, benzyl-, pyrazol-1-yl-methyl-, imidazol-4-yl-methyl-, pyrid-2-yl-methyl-, pyrid-3-yl-methyl- and thien-2-yl-methyl-;

provided that R$^2$ is other than t-butyl;

or a pharmaceutically acceptable salt thereof.

4. A compound as in claim 3, wherein
R¹ is selected from the group consisting of hydrogen, 2-(cyclohexyl), 2-(phenyl), 3-(phenyl), 4-(benzyl-oxy), 3-(piperidin-4-yl-oxy), 3-(piperidin-3R-yl-oxy) and 3-(piperidin-3S-yl-oxy);

is a ring structure selected from the group consisting of phenyl, 2-hydroxy-phenyl, 4-isopropyl-phenyl, 2-methoxy-phenyl, 3-methoxy-phenyl, 4-methoxy-phenyl, 5-methoxy-phenyl, 2-trifluoromethyl-phenyl, 3-trifluoromethyl-phenyl, 4-trifluoromethyl-phenyl, 4-methylsulfonyl-phenyl, 2-methyl-carbonyl-amino-phenyl, 4-methyl-carbonyl-amino-phenyl, 2,3-difluoro-phenyl, 3,4-difluoro-phenyl, 2,6-dimethyl-phenyl, 3,5-dimethyl-phenyl, 3,6-dimethyl-phenyl, 3,4-dimethoxy-phenyl, 3,5-dimethoxy-phenyl, 2,4,6-trimethyl-phenyl, 2,3,5,6,-tetramethyl-phenyl, naphth-1-yl, naphtha-2-yl, 2-hydroxy-naphth-1-yl, 2-fluoro-naphth-1-yl, 4-fluoro-naphth-1-yl, 4-methyl-naphth-1-yl, 2-methoxy-naphth-1-yl, 2-(methoxy-methyl)-naphth-1-yl, 9H-fluoren-2-yl, isoquinolin-4-yl, isoquinolin-5-yl, benzofur-5-yl, benzothiophen-5-yl, benzo[1,3]dioxol-5-yl and 2,3,-dihydro-benzo[1,4]dioxin-6-yl;
n is an integer selected from 0 and 1;
R² is selected from the group consisting of ethyl, n-propyl, isopropyl, n-butyl, isobutyl, hydroxy-methyl, hydroxy-ethyl, n-buten-3-yl, propyn-2-yl, amino-n-propyl-, cyclopropyl-methyl, benzyl, pyrazol-1-yl-methyl-, imidazol-4-yl-methyl-, pyrid-2-yl-methyl-, pyrid-3-yl-methyl- and thien-2-yl-methyl-;
or a pharmaceutically acceptable salt thereof.

5. A compound as in claim 4, wherein
R¹ is selected from the group consisting of hydrogen, 2-(phenyl), 3-(phenyl), 4-(benzyl-oxy), 3-(piperidin-4-yl-oxy), 3-(piperidin-3R-yl-oxy) and 3-(piperidin-3S-yl-oxy);

is a ring structure selected from the group consisting of phenyl, 2-hydroxy-phenyl, 4-isopropyl-phenyl, 3-methoxy-phenyl, 4-methoxy-phenyl, 5-methoxy-phenyl, 3-trifluoromethyl-phenyl, 2-methyl-carbonyl-amino-phenyl, 4-methyl-carbonyl-amino-phenyl, 2,3-difluoro-phenyl, 3,4-difluoro-phenyl, 2,6-dimethyl-phenyl, 3,5-dimethyl-phenyl, 2,4,6-trimethyl-phenyl, naphth-1-yl, 2-fluoro-naphth-1-yl, 4-fluoro-naphth-1-yl, 4-methyl-naphth-1-yl, 9H-fluoren-2-yl, isoquinolin-5-yl, benzofur-5-yl, benzothiophen-5-yl and 2,3,-dihydro-benzo[1,4]dioxin-6-yl;
n is an integer selected from 0 and 1;
R² is selected from the group consisting of ethyl, n-propyl, n-butyl, hydroxy-ethyl, n-buten-3-yl, propyn-2-yl, pyrazol-1-yl-methyl-, imidazol-4-yl-methyl-, and thien-2-yl-methyl-; and wherein the starred stereo-center is in the (S) stereo-configuration;
or a pharmaceutically acceptable salt thereof.

6. A compound as in claim 5, wherein
R¹ is selected from the group consisting of hydrogen, 3-(phenyl), 4-(benzyl-oxy), 3-(piperidin-4-yl-oxy), 3-(piperidin-3R-yl-oxy) and 3-(piperidin-3S-yl-oxy);

is a ring structure selected from the group consisting of phenyl, 4-isopropyl-phenyl, 4-methoxy-phenyl, 5-methoxy-phenyl, 3,4-difluoro-phenyl, 2,6-dimethyl-phenyl, 3,5-dimethyl-phenyl, naphth-1-yl, and 9H-fluoren-2-yl;
n is an integer selected from 0 and 1;
R² is selected from the group consisting of ethyl, n-propyl, hydroxy-ethyl, n-buten-3-yl, propyn-2-yl, imidazol-4-yl-methyl- and thien-2-yl-methyl-;
and wherein the starred stereo-center is in the (S) configuration;
or a pharmaceutically acceptable salt thereof.

7. A compound as in claim 6, wherein
R¹ is selected from the group consisting of hydrogen, 3-(phenyl) and 3-(piperidin-4-yl-oxy);

is a ring structure selected from the group consisting of phenyl, 4-methoxy-phenyl and 3,4-difluoro-phenyl;
n is 1;
R² is selected from the group consisting of ethyl, propyn-2-yl, imidazol-4-yl-methyl- and thien-2-yl-methyl-;
and wherein the starred stereo-center is in the (S) configuration;
or a pharmaceutically acceptable salt thereof.

8. A compound as in claim 1, wherein the starred stereo-center is present in an enantiomeric excess of the (S)-stereo-configuration.

9. A pharmaceutical composition comprising a pharmaceutically acceptable carrier and a compound of claim 1.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

* * * * *